US011242406B2

(12) United States Patent
Hamilton et al.

(10) Patent No.: US 11,242,406 B2
(45) Date of Patent: Feb. 8, 2022

(54) METHODS FOR THE TREATMENT OF A CANCER OR FIBROTIC DISORDER ASSOCIATED WITH MENA OR MENA(INV) BY ADMINISTERING A MAP KINASE INHIBITOR

(71) Applicant: METASTAT, INC., Boston, MA (US)

(72) Inventors: Douglas A. Hamilton, Boston, MA (US); Anna L. Blois, Boston, MA (US)

(73) Assignee: METASTAT, INC., Boston, MA (US)

( * ) Notice: Subject to any disclaimer, the term of this patent is extended or adjusted under 35 U.S.C. 154(b) by 438 days.

(21) Appl. No.: 16/312,988

(22) PCT Filed: Jul. 7, 2017

(86) PCT No.: PCT/US2017/041243
§ 371 (c)(1),
(2) Date: Dec. 21, 2018

(87) PCT Pub. No.: WO2018/009896
PCT Pub. Date: Jan. 11, 2018

(65) Prior Publication Data
US 2019/0225707 A1    Jul. 25, 2019

Related U.S. Application Data

(60) Provisional application No. 62/508,892, filed on May 19, 2017, provisional application No. 62/488,464, filed on Apr. 21, 2017, provisional application No. 62/469,373, filed on Mar. 9, 2017, provisional application No. 62/360,190, filed on Jul. 8, 2016.

(51) Int. Cl.
| | | |
|---|---|---|
| C07K 16/40 | (2006.01) | |
| A61P 35/00 | (2006.01) | |
| A61P 35/02 | (2006.01) | |
| A61K 9/00 | (2006.01) | |
| C07K 7/00 | (2006.01) | |
| C07K 16/28 | (2006.01) | |
| A61K 39/395 | (2006.01) | |
| A61K 31/337 | (2006.01) | |
| A61P 9/00 | (2006.01) | |
| A61K 31/5377 | (2006.01) | |
| A61K 31/7105 | (2006.01) | |
| G01N 33/50 | (2006.01) | |
| A61K 31/167 | (2006.01) | |
| A61K 31/166 | (2006.01) | |

(52) U.S. Cl.
CPC ............ *C07K 16/40* (2013.01); *A61K 9/0019* (2013.01); *A61K 9/0053* (2013.01); *A61K 31/337* (2013.01); *A61K 31/5377* (2013.01); *A61K 31/7105* (2013.01); *A61K 39/395* (2013.01); *A61P 9/00* (2018.01); *A61P 35/00* (2018.01); *A61P 35/02* (2018.01); *C07K 16/2896* (2013.01); *G01N 33/5011* (2013.01); *A61K 31/166* (2013.01); *A61K 31/167* (2013.01); *C07K 7/00* (2013.01); *C07K 2317/76* (2013.01)

(58) Field of Classification Search
CPC ........ C07K 16/40; C07K 7/00; A61K 31/337; A61K 9/0019; A61K 9/0053; A61K 31/5377; A61K 31/7105; A61P 35/00; A61P 35/02
See application file for complete search history.

(56) References Cited

U.S. PATENT DOCUMENTS

| | | |
|---|---|---|
| 2002/0048813 A1 | 4/2002 | Gertler et al. |
| 2013/0004424 A1 | 1/2013 | Gertler et al. |
| 2015/0044234 A1 | 2/2015 | Gertler et al. |
| 2015/0079113 A1 | 3/2015 | Gertler et al. |
| 2016/0184383 A1 | 6/2016 | Lalaoui et al. |
| 2017/0168056 A1 | 6/2017 | Gertler et al. |

FOREIGN PATENT DOCUMENTS

| | | |
|---|---|---|
| WO | 2010/068692 A1 | 6/2010 |
| WO | 2015/164862 A1 | 10/2015 |
| WO | 2015/173788 A1 | 11/2015 |

OTHER PUBLICATIONS

Kannaiyan R and Mahadevan D. (Dec. 2018) Expert Rev Anticancer Ther. 18(12): 1249-1270. (doi: 10. 1080/14737140.2018. 1527688).*
Hayess, K., et al., "Effect of Protein Kinase Inhibitors on Activity of Mammalian Small Heat-Shock Protein (HSP25) Kinase," Biochemical Pharmacology, vol. 53, Issue 9, pp. 1239-1247 (May 9, 1997).
Intentional Search Report of PCT/US2017/041243 dated Oct. 13, 2017.
Written Opinion of PCT/US2017/041243 dated Oct. 13, 2017.

(Continued)

*Primary Examiner* — Robert S Landsman
(74) *Attorney, Agent, or Firm* — Christopher M. Cabral; Much Shelist PC

(57) ABSTRACT

Phosphorylation and dephosphorylation of MENA and MENA isoforms regulates the metastatic activity of cancer cells. Administration of a MENA kinase inhibitor results in significant reduction in the development of cancer metastasis in established and developing tumors. Administration of a MENA kinase inhibitor in conjunction with a tyrosine kinase inhibitor enhances efficacy of tyrosine kinase inhibitor therapy. Administration of a MENA kinase inhibitor in conjunction with anti-microtubule agent results in significant reduction in chemotherapy-induced tumor cell dissemination and enhances efficacy of anti-microtubule therapy.

13 Claims, 11 Drawing Sheets

Specification includes a Sequence Listing.

(56) References Cited

OTHER PUBLICATIONS

DiModugno, et al., "Splicing Program of Human MENA Produces a Previously Undescribed Isoform Associated with Invasive, Mesenchymal-like Breast Tumors," Proceedings of the National Academy of Sciences USA, vol. 109, No. 47, op. 19280-19285 (Nov. 20, 2012).
Garuti, et al., "Non-ATP Competitive Protein Kinase Inhibitors," Current Medicinal Chemistry, vol. 17, No. 25, pp. 2804-2821 (Jan. 1, 2010) (Abstract).
Philippar, et al., "A Mena Invasion Isoform Potentiates EGF-Induced Carcinoma Cell Invasion and Metastasis," Development Cell, vol. 15, No. 6, pp. 813-828 (Dec. 31, 2008).
Pozo, et al., "Inhibition of DYRK1A Destabilizeds EGFR and Reduces EGFR-Dependent Glioblastoma Growth," Journal of Clinical Investigation, vol. 123, No. 6, pp. 2475-2487 (May 1, 2013).
Blois, A., et al., "MenaINV a Novel Therapeutic Target for Prevention and Treatment of Metastatic Disease," Poster Presentation, Jun. 2018.

\* cited by examiner

METHODS FOR THE TREATMENT OF A CANCER OR FIBROTIC DISORDER ASSOCIATED WITH MENA OR MENA(INV) BY ADMINISTERING A MAP KINASE INHIBITOR

CROSS-REFERENCE TO RELATED APPLICATIONS

The present application is the 35 U.S.C. § 371 National Stage of International Application Number PCT/US2017/041243 filed Jul. 7, 2017, which claims the benefit of U.S. Provisional Application No. 62/360,190 filed Jul. 8, 2016; U.S. Provisional Application No. 62/469,373 filed Mar. 9, 2017, U.S. Provisional Application No. 62/488,464 filed Apr. 21, 2017; and U.S. Provisional Application No. 62/508,892 filed May 19, 2017, the contents of each which are incorporated herein by reference.

INCORPORATION OF SEQUENCE LISTING

A Sequence Listing is provided herewith as a text file entitled "010739-5005-WO-Sequence-Listing.txt" created on Jul. 7, 2017 and having a size of 24 KB. The contents of the text file are incorporated by reference herein in their entirety.

FIELD OF THE INVENTION

The present invention comprises compositions for inhibiting cancer metastasis and fibrotic disease by modulating activity of MENA kinases.

BACKGROUND OF THE INVENTION

Cancer is a complex disease characterized most simply by uncontrolled growth and spread of abnormal cells. Cancer remains one of the world's most serious health problems and is the second most common cause of death in the United States after heart disease. When cancer is detected at an early stage most patients have a favorable prognosis. Patients with advanced cancer that has progressed to the metastatic disease stage generally have a poor prognosis and such cancers account for approximately 90% of all cancer related deaths. Current oncological therapy and the development of new therapeutics have focused on inhibition of cancer cell proliferation through anti-proliferative cytotoxic or targeted therapies aimed at the primary tumor.

The development of effective anti-metastatic therapies that could generally inhibit metastatic progression could substantially improve patient outcome and survival. Since the process that drives the dissemination of malignant cells is shared among cancers, drugs that inhibit the metastatic cascade will be broadly beneficial across multiple cancer indications. Currently available anti-metastatic drugs fall into two general categories; anti-vascular (angiogenesis) and matrix metalloproteinase (MMPs) inhibitors. The main limitation of these drugs has been a lack of efficacy and indiscriminant molecular inhibition.

What is lacking are effective therapies that target tumor cell migration, intravasation and metastasis thereby arresting the primary tumor in a state of indolence which can be subsequently targeted with existing approaches.

The MENA protein and its isoforms have been implicated in the sequential, multi-step process of metastasis and has been shown to be involved in intravasation and the motility of tumor cells. MENA is a member of the Ena/VASP family of proteins, which plays a key regulatory role in actin polymerization. MENA deficiency in the PyMT mouse breast cancer model suppresses intravasation, eliminates mortality and morbidity, and greatly reduces the frequency of metastatic dissemination to the lung. Expression of MENA$^{INV}$ in a xenograft mouse mammary tumor promotes increased formation of spontaneous lung metastases from orthotopic tumors and alters the sensitivity of tumor cells to epidermal growth factor (EGF), hepatocyte growth factor (HGF) and insulin-like growth factor (IGF) among others.

In patients, high levels of MENA expression correlates with increased metastatic risk which has been observed in tumor samples from patients with early stage disease that subsequently develop cancer metastasis. High levels of MENA expression is associated with increased risk of cancer metastasis in patients with early stage breast cancer, squamous cell carcinoma of the lung, cervical, colorectal and pancreatic cancer. MENA is alternately spliced to give rise to multiple protein isoforms that are differentially expressed during tumor progression. Two of the best characterized isoforms are MENA$^{INV}$, expressed exclusively in invasive tumor cells, and MENA$^{11a}$, an epithelial-specific isoform expressed in primary breast carcinomas and down-regulated in invasive tumor cells. MENA$^{INV}$ expression confers a potent pro-metastatic phenotype when expressed in breast cancer cells by potentiating their chemotactic response to epidermal growth factor (EGF), thereby enhancing their ability to engage in efficient streaming motility via increasing their paracrine signaling with macrophages. Conservation of MENA up-regulation in invasive tumor cells across species and different tumor types suggests that it plays a crucial role in metastatic progression.

MENA consists of at least four commonly recognized domains, including EVH1 which facilitates localization, an LERER motif, followed by a proline rich sequence involved in profilin binding, followed by a series of actin binding motifs within the EVH2 domain which is followed by an oligomerization motif. The arrangement of these domains is illustrated in FIG. 1. The MENA$^{INV}$ isoform is formed through alternative splicing of an exon into the MENA mRNA transcript which results in the insertion of a 19 amino acid segment at position 116, just after the EVH1 domain of the protein. The MENA$^{11a}$ isoform is generated through alternative splicing of an exon into the MENA mRNA transcript which inserts a 21 amino acid segment at position 513, within the EVH2 domain of the MENA protein.

The present invention reduces the activity of MENA and MENA isoforms to drive aggressive cancer to spread from the primary tumor to distant sites of metastasis and to block excessive fibrogen deposition associated with fibrotic disease. The present invention alleviates the MENA-dependent phenotypes associated with cancer metastasis, tumor cell drug resistance and fibrogen deposition by reducing the presence or activity of the MENA$^{INV}$ isoform, increasing the presence or activity of the MENA$^{11a}$ isoform, and or by inhibiting the ability of kinase inhibitors from the Ras-Raf-MEK-MAPK/ERK and PI3K-AKT/mTOR pathways to modulate the activity of MENA or MENA isoforms. The present invention also increases the efficacy of anti-tumor tyrosine kinase inhibitors (TKIs) and or anti-microtubule drugs when administered in combination with drugs that reduce the presence or activity of MENA or the MENA$^{INV}$ isoform, increase the presence or activity of the MENA$^{11a}$ isoform, and or inhibit the ability of kinases from the Ras-Raf-MEK-MAPK/ERK and PI3K-AKT/mTOR pathways to modulate the activity of MENA or MENA isoforms.

The MENA protein acts via multiple processes that are important for tumor cell invasion and metastasis, actin polymerization, adhesion, and EGF-elicited motility responses. Highly migratory and invasive tumor cell subpopulations produce MENA mRNAs that contain alternative splice forms of MENA. One such alternative splice form, MENA$^{INV}$ is prognostic for risk of cancer metastasis, described in U.S. Patent Application Publication No. 2012/0028252 which is incorporated herein by reference in its entirety. Another alternative splice form, MENA$^{11a}$, is described in U.S. Patent Application Publication No. 2010/0047240 which is incorporated herein by reference in its entirety. Methods and compositions for identifying the various MENA isoforms and differentiating one from the other are described in U.S. Patent Application Publication No. 2010/0033258 which is also incorporated herein by reference in its entirety.

The MENA protein acts via multiple processes that are important for tumor cell invasion and metastasis, actin polymerization, adhesion, and EGF-elicited motility responses. Highly migratory and invasive tumor cell subpopulations produce MENA mRNAs that contain alternative splice forms of MENA. One such alternative splice form, MENA$^{INV}$ is prognostic for risk of cancer metastasis, described in U.S. Patent Application Publication No. 2012/0028252 which is incorporated herein by reference in its entirety. Another alternative splice form, MENA$^{11a}$, is described in U.S. Patent Application Publication No. 2010/0047240 which is incorporated herein by reference in its entirety. Methods and compositions for identifying the various MENA isoforms and differentiating one from the other are described in U.S. Patent Application Publication No. 2010/0033258 which is also incorporated herein by reference in its entirety.

The MENA protein acts via multiple processes that are important for tumor cell invasion and metastasis, actin polymerization, adhesion, and EGF-elicited motility responses. Highly migratory and invasive tumor cell subpopulations produce MENA mRNAs that contain alternative splice forms of MENA. One such alternative splice form, MENA$^{INV}$ is prognostic for risk of cancer metastasis, described in U.S. Patent Application Publication No. 2012/0028252 which is incorporated herein by reference in its entirety. Another alternative splice form, MENA$^{11a}$, is described in U.S. Patent Application Publication No. 2010/0047240 which is incorporated herein by reference in its entirety. Methods and compositions for identifying the various MENA isoforms and differentiating one from the other are described in U.S. Patent Application Publication No. 2010/0033258 which is also incorporated herein by reference in its entirety.

The present invention arises in part from the observation that MENA plays a role in regulating phosphotyrosine receptor signaling. Some cancers do not respond at all or weakly respond to treatments comprising tyrosine kinase inhibitors (TKIs). Many cancers develop resistance to treatments comprising tyrosine kinase inhibitors (TKIs) that initially reduce tumor cell growth and proliferation but eventually lose efficacy. The discovery that MENA$^{INV}$ blocks dephosphorylation of at least one TKI target receptor protein (EGFR), by limiting the ability of endogenous dephosphorylases such as PTP1B to desensitize the target receptor to stimulation by its cognate ligand, suggests a model for why the MENA$^{INV}$ isoform is highly correlated with invasive cancer phenotypes. In this model MENA$^{INV}$ sensitizes tumor cells to growth factor stimulation by disrupting the normal down-regulation of induced receptors by dephosphorylation by disrupting the association of the dephosphorylase complex with the target receptor. In contrast, the MENA$^{11a}$ isoform is down-regulated in invasive tumor cells and expression of MENA$^{11a}$ correlates with cohesive tumor morphology. Any treatment to reduce the presence or activity of the MENA or MENA$^{INV}$ isoform, or alternatively, increase the presence or activity of the MENA$^{11a}$ isoform may provide a method for limiting or eradicating development of a metastatic cancer and or fibrotic disease phenotype. Furthermore, reducing the presence or activity of MENA or MENA$^{INV}$ and or increasing the presence or activity of MENA$^{11a}$ may improve and prolong the efficacy of current TKI-based therapies. One potential method for modulating MENA isoform activity is by regulating phosphorylation and dephosphorylation of MENA and or MENA isoforms by inhibiting MENA kinase activity.

The present invention is also based in part on the discovery that the peptide sequence proximal to the serine 125 (Ser125) phosphorylation site of MENA and the equivalent serine 144 (Ser144) phosphorylation site of MENA$^{INV}$ are potent substrates of the MAPKAPK2/MK2 kinase. Replacement of Ser125 in MENA and or Ser144 in MENA$^{INV}$ with a non-phosphorylable amino acid changes the peptide substrates to effective peptide inhibitors of the MAPKAPK2/MK2 kinase. Hayess and Benndorf discovered the peptide sequence KKKALHRQLGVAA (SEQ ID NO: 30) is a potent inhibitor of MAPKAPK2/MK2 and is based on the consensus sequence binding domain for the MAPKAPK2/MK2 substrate heat shock protein HSP25/27. Mass spec phosphoproteomic analysis of MAPKAPK2/MK2-depedent phosphorylation demonstrated that MENA/MENA$^{INV}$ are more potent MAPKAPK2/MK2 substrates compared to HSP27. In doxorubicin treated cells the MENA Ser125 phosphorylation site becomes more heavily phosphorylated (~8× increase) than the HSP27 Ser82 phosphorylation site (~2.5× increase). The Ser125/Ser144 serine residue was replaced with a non-phosphorylatable glycine residue to convert the MENA/MENA$^{INV}$ substrate peptides into effective MENA kinase inhibitors.

DETAILED DESCRIPTION OF THE INVENTION

Figure 1:
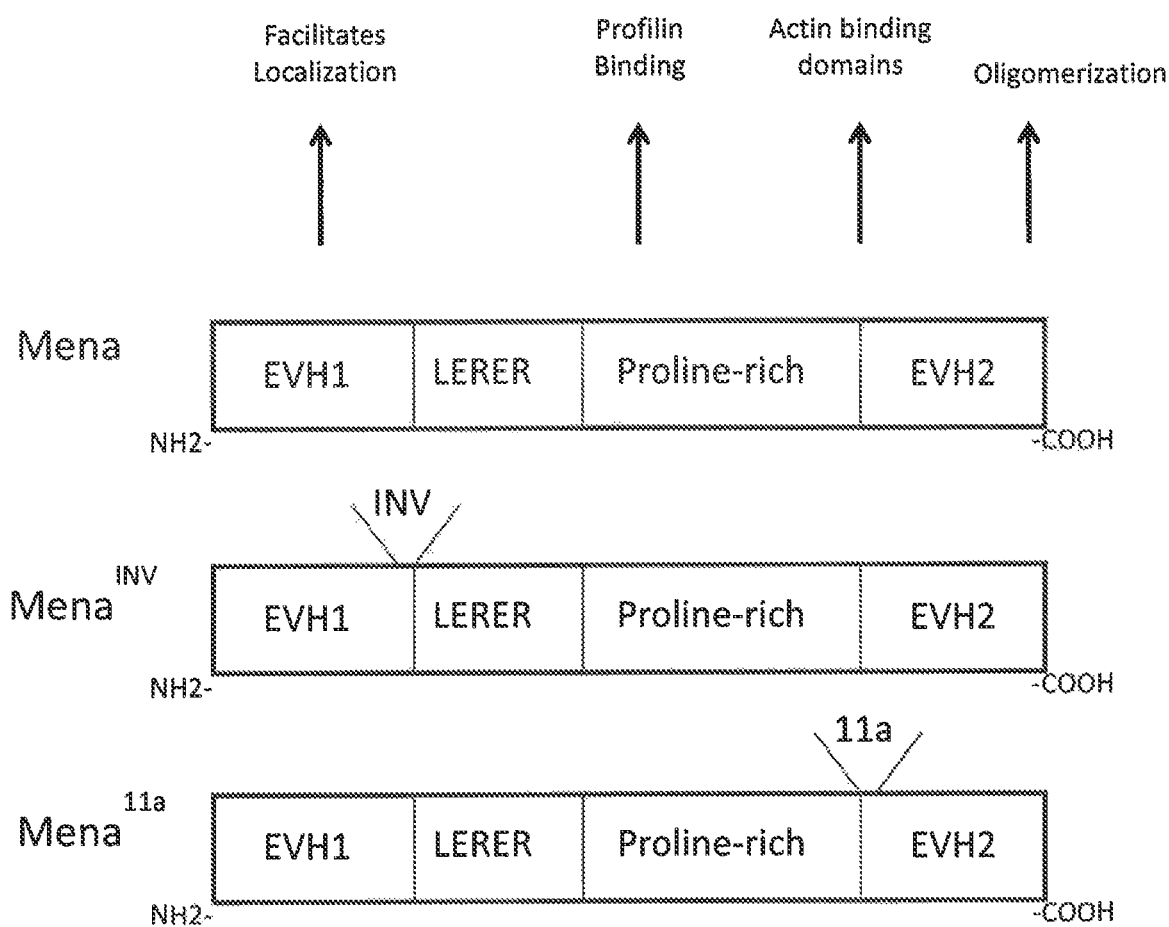
FIG. 1 represents an alignment of MENA protein isoforms with the functions of individual domains identified. The relative location of the 19 amino acid insertion characteristic of MENA$^{INV}$ is indicated by "\INV/" and the relative location of the 23 amino acid insertion of MENA$^{11a}$ is indicated by "\11a".

A method is provided for treating cancer in a patient with a solid tumor comprimising reducing the presence or activity of the MENA and or MENA$^{INV}$ isoform of MENA in a subject and may further comprise increasing the presence or activity of the MENA$^{11a}$ isoform in a subject. The method involves inhibition of the phosphorylation or dephosphorylation of MENA and or the MENA$^{INV}$ protein isoform by administration of a drug that inhibits the transfer of phosphate groups to serine, threonine, and/or tyrosine residues in the MENA and or MENA$^{INV}$ isoform substrate by a MENA kinase. Similarly, the method involves activation of the phosphorylation or dephosphorylation of the MENA$^{11a}$ isoform substrate. The method may involve administration of MENA- and or MENA$^{INV}$- and MENA$^{11a}$-specific drugs as described herein to simultaneously reduce the presence or activity of MENA and or MENA$^{INV}$ and increase the presence or activity of MENA$^{11a}$. As used herein, the term "MENA kinase inhibitor" refers to any composition which inhibits phosphorylation or dephosphorylation of a MENA isoform, including but not limited to MENA, MENA$^{INV}$, and MENA$^{11a}$.

In an embodiment of the present invention the MENA kinase inhibitor is a small molecule, peptide, protein, antibody, monoclonal antibody, antibody fragment, RNA aptamer, ribozyme, or siRNA.

In an embodiment the MENA kinase inhibitor is an ATP-competitive inhibitor. In another embodiment the MENA kinase inhibitor is a non-ATP competitive inhibitor.

In an embodiment the MENA kinase inhibitor is a reversible inhibitor. In another embodiment the MENA kinase inhibitor is a non-reversible covalent inhibitor.

In an embodiment the MENA kinase inhibitor is an inhibitor of the Ras-Raf-MEK-ERK and or PI3K-PTEN-ATk-mTOR pathways. Including, but not limited to Raf, p38 MAP, MEK, MAPK, PKD-1, PI3K, Akt, and mTOR inhibitors or a similar protein kinase inhibitors familiar to persons skilled in the art.

In an embodiment the MENA kinase inhibitor is an inhibitor of the MAPK-activated protein kinase (MAPK kinase). As used herein the term "MAPK kinase" collectively refers to each and all of the several MAPK-activated protein kinases including, but not limited to MAPK-activated protein kinase 2 (MAPKAPK2 or MK2) inhibitor, MAPK-activated protein kinase 3 (MAPKAPK3 or MK3) inhibitor, MAPK-activated protein kinase 5 (MAPKAPK5 or MK5) inhibitor, or similar MAPK-activated protein kinase inhibitors familiar to persons skilled in the art. In a preferred embodiment the MENA kinase inhibitor specifically inhibits MAPKAPK2 (MK2).

In an embodiment the MENA kinase inhibitor reduces or eliminates phosphorylation of one or more of Ser2, Ser5, Tyr16, Ser29, Thr30, Ser33, Tyr38, Thr41, Thr45, Tyr70, Thr74, Thr76, Tyr87, Ser93, Ser102, Ser113, Thr116, Thr119, Ser125, Ser136, Ser265, Ser266, Ser272, Thr275, Ser279, Ser284, Ser285, Ser287, Ser295, Thr300, Ser302, Ser327, Ser344, Thr345, Ser375, Ser381, Ser383, Thr390, Ser405, Thr410, Ser411, Ser414, Ser423, Ser425, Ser426, Thr428, Thr430, Ser442, Ser444, Ser449, Ser463, Thr464, Thr467, Ser477, Ser481, Ser482, Ser485, Ser486, Thr487, Ser488, Thr489, Thr493, Thr500, Thr502, Ser506, Ser508, Ser512, Ser516, Thr517, Ser520, Ser523, Tyr534, Ser550, Ser565, Ser567, or Thr569 amino acids in MENA (SEQ ID NO.: 1). In a preferred embodiment the MENA kinase inhibitor eliminates phosphorylation of Ser125 of the MENA protein.

In another embodiment the MENA kinase inhibitor reduces or eliminates dephosphorylation of one or more of phosphorylated Ser2, Ser5, Tyr16, Ser29, Thr30, Ser33, Tyr38, Thr41, Thr45, Tyr70, Thr74, Thr76, Tyr87, Ser93, Ser102, Ser113, Thr116, Thr119, Ser125, Ser136, Ser265, Ser266, Ser272, Thr275, Ser279, Ser284, Ser285, Ser287, Ser295, Thr300, Ser302, Ser327, Ser344, Thr345, Ser375, Ser381, Ser383, Thr390, Ser405, Thr410, Ser411, Ser414, Ser423, Ser425, Ser426, Thr428, Thr430, Ser442, Ser444, Ser449, Ser463, Thr464, Thr467, Ser477, Ser481, Ser482, Ser485, Ser486, Thr487, Ser488, Thr489, Thr493, Thr500, Thr502, Ser506, Ser508, Ser512, Ser516, Thr517, Ser520, Ser523, Tyr534, Ser550, Ser565, Ser567, or Thr569 amino acids in MENA (SEQ ID NO.: 1). In a preferred embodiment the MENA kinase inhibitor eliminates dephosphorylation of phosphorylated Ser125 of the MENA protein.

In an embodiment the MENA kinase inhibitor reduces or eliminates phosphorylation of one or more of Ser3, Thr6, Thr8, Ser11, Thr12 of the MENA INV exon (SEQ ID NO.:2), or amino acids proximally flanking the MENA$^{INV}$ exon sequence at positions 117-135 of the MENA$^{INV}$ protein (SEQ ID NO.: 3). In a preferred embodiment the MENA kinase inhibitor reduces or eliminates phosphorylation of Ser144 of the MENA$^{INV}$ protein isoform.

In an embodiment the MENA kinase inhibitor reduces or eliminates phosphorylation of one or more of Ser2, Ser5, Tyr16, Ser29, Thr30, Ser33, Tyr38, Thr41, Thr45, Tyr70, Thr74, Thr76, Tyr87, Ser93, Ser102, Ser113, Thr116, Ser119, Thr122, Thr124, Ser127, Thr128, Thr138, Ser144, Ser155, Ser284, Ser285, Ser306, Thr294, Ser303, Ser304, Ser306, Ser134, Thr319, Ser321, Ser346Ser363, Thr364, Ser394, Ser400, Ser402, Ser409, Ser424, Thr429, Ser430, Ser433, Ser442, Ser444, Ser445, Thr447, Thr449, Ser461, Ser468, Ser482, Thr483, Thr486, Ser496, Thr500, Ser501, Ser504, Ser505, Thr506, Ser507, Thr508, Thr512, Thr519, Thr521, Ser525, Ser527, Ser531, Ser535, Thr536, Ser539, Ser542, Thr548, Tyr553, Thr569, ser584, Ser586, or Thr588 amino acids in MEAN$^{INV}$ (SEQ ID NO.: 3). In a preferred embodiment the MENA kinase inhibitor eliminates phosphorylation of Ser144 of the MENA$^{INV}$ protein isoform.

In an embodiment the MENA kinase inhibitor reduces or eliminates dephosphorylation of one or more of phosphorylated Ser3, Thr6, Thr8, Ser11, Thr12 of the MENA INV exon (SEQ ID NO.: 2), or phosphorylated amino acids proximally flanking the MENA$^{INV}$ exon sequence at positions 117-135 of the MENA$^{INV}$ protein (SEQ ID NO.: 3). In a preferred embodiment the MENA kinase inhibitor reduces or eliminates dephosphorylation of phosphorylated Ser144 of the MENA$^{INV}$ protein isoform.

In an embodiment the MENA kinase inhibitor reduces or eliminates phosphorylation of one or more of phosphorylated Ser2, Ser5, Tyr16, Ser29, Thr30, Ser33, Tyr38, Thr41, Thr45, Tyr70, Thr74, Thr76, Tyr87, Ser93, Ser102, Ser113, Thr116, Ser119, Thr122, Thr124, Ser127, Thr128, Thr138, Ser144, Ser155, Ser284, Ser285, Ser306, Thr294, Ser303, Ser304, Ser306, Ser134, Thr319, Ser321, Ser346Ser363, Thr364, Ser394, Ser400, Ser402, Ser409, Ser424, Thr429, Ser430, Ser433, Ser442, Ser444, Ser445, Thr447, Thr449, Ser461, Ser468, Scr482, Thr483, Thr486, Ser496, Thr500, Ser501, Ser504, Ser505, Thr506, Ser507, Thr508, Thr512, Thr519, Thr521, Ser525, Ser527, Ser531, Ser535, Thr536, Ser539, Ser542, Thr548, Tyr553, Thr569, ser584, Ser586, or Thr588 amino acids in MENA$^{INV}$ (SEQ ID NO.: 3). In a preferred embodiment the MENA kinase inhibitor eliminates dephosphorylation of phosphorylated Ser144 of the MENA$^{INV}$ protein isoform.

In an embodiment the MENA kinase inhibitor reduces or eliminates phosphorylation of one or more of Ser3, Ser15, Tyr16, Ser18 of the MENA$^{11a}$ exon (SEQ ID NO.: 4), amino acids proximally flanking the MENA$^{11a}$ exon sequence at positions 514-534 of the MENA$^{11a}$ protein (SEQ ID NO.: 5), or Ser125 of SEQ ID NO.:5.

In an embodiment the MENA kinase inhibitor reduces or eliminates phosphorylation of one or more of Ser2, Ser5, Tyr16, Ser29, Thr30, Ser33, Tyr38, Thr41, Thr45, Tyr70, Thr74, Thr76, Tyr87, Ser93, Ser102, Ser113, Thr116, Thr119, Ser125, Ser136, Ser265, Ser266, Ser272, Thr275, Ser279, Ser284, Ser285, Ser287, Ser295, Thr300, Ser302, Ser327, Ser344, Thr345, Ser375, Ser381, Ser383, Thr390, Ser405, Thr410, Ser411, Ser414, Ser423, Ser425, Ser426, Thr428, Thr430, Ser442, Ser444, Ser463, Thr464, Ser477, Thr481, Ser482, Ser485, Ser486, Thr487, Ser488, Thr489, Thr493, Thr500, Thr502, Ser506, Ser508, Ser512, Ser516, Ser528, Tyr529, Ser531, Ser537, Thr538, Ser541, Ser544, Thr550, Tyr555, Thr571, Ser586, Ser588, or Thr590 amino acids in MENA$^{11a}$ (SEQ ID NO.: 5). In a preferred embodiment the MENA kinase inhibitor eliminates phosphorylation of Ser125 of the MENA$^{11a}$ protein isoform.

In an embodiment the MENA kinase inhibitor reduces or eliminates dephosphorylation of one or more of phosphorylated Ser3, Ser15, Tyr16, Ser18 of the MENA$^{11a}$ exon (SEQ ID NO.: 4), phosphorylated amino acids proximally flanking the MENA$^{11a}$ exon sequence at positions 514-534 of SEQ ID NO.: 5, or Ser125 of SEQ ID NO.: 5.

In an embodiment the MENA kinase inhibitor reduces or eliminates dephosphorylation of one or more of phosphorylated Ser2, Ser5, Tyr16, Ser29, Thr30, Ser33, Tyr38, Thr41, Thr45, Tyr70, Thr74, Thr76, Tyr87, Ser93, Ser102, Ser113, Thr116, Thr119, Ser125, Ser136, Ser265, Ser266, Ser272, Thr275, Ser279, Ser284, Ser285, Ser287, Ser295, Thr300, Ser302, Ser327, Ser344, Thr345, Ser375, Ser381, Ser383, Thr390, Ser405, Thr410, Ser411, Ser414, Ser423, Ser425, Ser426, Thr428, Thr430, Ser442, Ser444, Ser463, Thr464, Ser477, Thr481, Ser482, Ser485, Ser486, Thr487, Ser488, Thr489, Thr493, Thr500, Thr502, Ser506, Ser508, Ser512, Ser516, Ser528, Tyr529, Ser531, Ser537, Thr538, Ser541, Ser544, Thr550, Tyr555, Thr571, Ser586, Ser588, or Thr590 amino acids in MENA$^{11a}$ (SEQ ID NO.: 5). In a preferred embodiment the MENA kinase inhibitor eliminates dephosphorylation of phosphorylated Ser125 of the MENA$^{11a}$ protein.

In an embodiment the MENA kinase inhibitor is a small molecule inhibitor that specifically inhibits phosphorylation or dephosphorylation of MENA or a MENA isoform kinase.

In some embodiments the small molecule MENA kinase inhibitor is based on scaffolds, such as aminocyoanopyridine, pyrazolopyrimidines, pyrrolopyridine, carboline, pyrrolopyrimidone, and CMPD 1. In preferred embodiments the small molecule inhibitor specifically inhibits phosphorylation or dephosphorylation of MENA and or a MENA isoform by MENA kinase.

In an embodiment the MENA kinase inhibitor is a peptide inhibitor that specifically inhibits phosphorylation or dephosphorylation of MENA and or a MENA isoform by MENA kinase.

In an embodiment of the present invention the MENA kinase inhibitor comprises at least one of the peptides LPRQNGQLP (SEQ ID NO: 6), LARQNGQLP (SEQ ID NO: 7), KALPRQNGQLP (SEQ ID NO: 8), and KALARQNGQLP (SEQ ID NO: 9).

In an embodiment the MENA kinase inhibitor is linked to a cell-penetrating peptide carrier sequence to facilitate uptake and delivery including, but not limited to HIV TAT peptide sequence. In certain embodiments the cell-penetrating carrier sequence based on the HIV TAT peptide sequence comprises at least one of the peptides YARAAARQARA (SEQ ID NO: 10), and YGRKKRRQRRR (SEQ ID NO: 11). Other cell-penetrating carrier forms are expressly contemplated. For example, KAFAKLAARLYR (SEQ ID NO: 12) and FAKLAARLYR (SEQ IS NO: 13) based on the antithrombin III heparin-binding domain.

In certain embodiments the MENA kinase inhibitor comprises at least one of the peptides YARAAARQARALPRQNGQLP (SEQ ID NO: 14), YARAAARQARALARQNGQLP (SEQ ID NO: 15), YARAAARQARAKALPRQNGQLP (SEQ ID NO: 16), YARAAARQARAKALARQNGQLP (SEQ ID NO: 17), YGRKKRRQRRRLPRQNGQLP (SEQ ID NO: 18), YGRKKRRQRRRLARQNGQLP (SEQ ID NO: 19), YGRKKRRQRRRKALPRQNGQLP (SEQ ID NO: 20), YGRKKRRQRRRKALARQNGQLP (SEQ ID NO: 21), KAFAKLAARLYRKALPRQNGQLP (SEQ ID NO: 22), KAFAKLAARLYRKALARQNGQLP (SEQ ID NO: 23), KAFAKLAARLYRKAKALPRQNGQLP (SEQ ID NO: 24), KAFAKLAARLYRKAKALARQNGQLP (SEQ ID NO: 25) FAKLAARLYRKALPRQNGQLP (SEQ ID NO: 26), FAKLAARLYRKALARQNGQLP (SEQ ID NO: 27), FAKLAARLYRKAKALPRQNGQLP (SEQ ID NO: 28), and FAKLAARLYRKAKALARQNGQLP (SEQ ID NO: 29).

Peptides were synthesized using standard solid phase peptide chemistry with FMOC protected amino acids on resin. Amino acid activation and coupling was carried out with HBTU/HOBt and DIEA. FMOC groups are removed using 20% piperidine in DMF. The resin-bound sequence was then cleaved and deprotected with 80-90% TFA containing a variety of scavengers which can include water, thioanisole, ethylmethylsulfide, and ethanedithiol, and/or triisopropylsilane. Peptides were precipitated into ether and then isolated by centrifugation. The dried peptide pellets reconstituted in a water and acetonitrile mixture and lyophilized prior to purification by reverse phase HPLC on a C18 column, which was eluted with acetonitrile-water buffers containing 0.1% TFA. Each peptide is analyzed and pure fractions are pooled and lyophilized. Analytical HPLC data was obtained on a 5 micron C18 analytical column and eluted with water-acetonitrile buffers containing 0.1% TFA. Molecular weight was confirmed by MALDI-TOF analysis.

In an embodiment a medicament comprising a MENA kinase inhibitor is prophylactically administered to a subject in need thereof to prevent development of metastatic cancer or progression of fibrotic disease. A medicament comprising a MENA kinase inhibitor may also be administered therapeutically to reduce metastasis of an existing metastatic cancer.

In other embodiments a MENA kinase inhibitor may be administered prior to, in conjunction with, or subsequent to, administration of TKI therapeutics specific to receptor tyrosine kinases that target EGF receptor (EGFR), HER2/neu, c-SRC, hepatocyte growth factor receptor (HGFR), fibroblast growth factor receptor, insulin-like growth factor receptor (IGFR), platelet-derived growth factor receptor, vascular endothelial growth factor receptors, and other cancer associated targets known to those skilled in the art, to improve or prolong the efficacy of the TKI therapeutic. In addition, the MENA kinase inhibitor may be administered in conjunction with other mitogen activated protein kinase inhibitors.

In an embodiment a MENA kinase inhibitor is administered to treat a MENA-mediated disease or disorder, wherein the MENA-mediated disease or disorder is an autoimmune disorder, chronic or acute inflammatory disorder, auto-inflammatory disorder, a fibriotic disorder, a metabolic disorder, a neoplasia, or a cardiovascular or cerebrovascular disorder.

In further embodiment the fibriotic disorder is selected from the group consisting of systemic sclerosis/scleroderma, lupus nephritis, connective tissue disease, wound healing, surgical scarring, spinal cord injury, CNS scarring, acute lung injury, pulmonary fibrosis, idiopathic pulmonary fibrosis, cystic fibrosis, chronic obstructive pulmonary disease, adult respiratory distress syndrome, acute lung injury, drug-induced lung injury, glomerulonephritis, chronic kidney disease, diabetic nephropathy, hypertension-induced nephropathy, alimentary track or gastrointestinal fibrosis, renal fibrosis, hepatic or biliary fibrosis, liver fibrosis, nonalcoholic steatohepatitis, hepatitis C, hepatocellular carcinoma, cirrhosis, primary biliary cirrhosis, cirrhosis due to fatty liver disease cirrhosis due to alcoholic fatty liver disease, cirrhosis due to nonalcoholic steatosis/non-alcoholic fatty liver disease, radiation-induced fibrosis head and neck fibrosis, gastrointestinal fibrosis, pulmonary fibrosis, primary sclerosing cholangitis, restenosis, cardiac fibrosis, endomyocardial fibrosis, atrial fibrosis, ophthalmic scarring, fibrosclerosis, fibrotic cancers, fibroids, fibroma, fibroadenomas, fibrosarcomas, transplant mteriopathy, keloid, mediastinal fibrosis, myelofibrosis, retroperitoneal fibrosis, progressive massive fibrosis, and nephrogenic systemic fibrosis.

In further embodiment the neoplasia is selected from the group consisting of angiogenesis disorders, multiple myeloma, leukemias, acute lymphocytic leukemia, acute and chronic myelogenous leukemia, chronic lymphocytic leukemia, acute lymphoblastic leukemia, promyelocytic leukemia, lymphomas, B-cell lymphoma, T-cell lymphoma, mantle cell lymphoma, hairy cell lymphoma, Burkitt's lymphoma, mast cell tumors, Hodgkin's disease, non-Hodgkin's disease, myelodysplasia syndrome, fibrosarcoma, rhabdomyosarcoma; astrocytoma, neuroblastoma, glioma, schwannomas, melanoma, seminoma, teratocarcinoma, osteosarcoma, xenodenna pigmentosum, keratoctanthoma, thyroid follicular cancer, Kaposi's sarcoma, melanoma, teratoma, rhabdomyosarcoma, metastatic and bone disorders, cancer of the bone, mouth/pharynx, esophagus, larynx, stomach, intestine, colon, rectum, lung, liver, pancreas, nerve, brain, head and neck, throat, ovary, uterus, prostate, testis, bladder, kidney, breast, gall bladder, cervix, thyroid, prostate, and skin, non-small cell lung cancer, small cell lung cancer, glioma, and glioblastoma multiforme.

In further embodiment the cardiovascular or cerebrovascular disorder is selected from the group consisting of atherosclerosis, restenosis of an atherosclerotic coronary artery, acute coronary syndrome, myocardial infarction, cardiac-allograft vasculopathy, stroke, central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

In other embodiments a MENA kinase inhibitor may be administered prior to, in conjunction with, or subsequent to, administration of anti-microtubules drugs including but not limited to taxel, docetaxel, paclitaxel, albumin-bound paclitaxel or any other anti-microtubule associated drugs known to those skilled in the art.

EXAMPLES

The following examples illustrate the scope of the invention. Specific elements of the examples are for descriptive purposes only and are not intended to limit the scope of the invention. Those skilled in the art could develop equivalent methods and utilize comparable materials that are within the scope of the invention.

Example 1

MENA Isoform Phosphorylation and Related Reagents and Assays

MENA Isoforms are Differentially Phosphorylated.

Analysis of MENA$^{INV}$ in tumor cells found in TMEMs (Tumor Micro Environment of Metastasis) indicates that the protein is actively phosphorylated. Differences in phosphorylation between MENA$^{INV}$ and MENA suggest that the phosphorylated amino acids are associated with the 19 amino acids characteristic of MENA$^{INV}$ which are absent in MENA. Similar observations from analysis of non-metastatic tumor cells expressing MENA$^{11a}$ indicate that the 21 amino acids characteristic of that isoform of MENA may also represent targets for phosphorylation. Importantly, the effect on phosphorylation of each of the MENA isoform insertions (relative to MENA) may not be due only to phosphorylation of amino acids within the MENA$^{INV}$ and MENA$^{11a}$ sequences, but may affect phosphorylation of MENA amino acids in close proximity (spatially or in adjacent sequences) to the and MENA$^{11a}$ sequences.

To determine which of the potential amino acid residues associated with, or in proximity to, the MENA$^{INV}$ and MENA$^{11a}$ insertions may be phosphorylated, a series of recombinant MENA$^{INV}$ and MENA$^{11a}$ constructs was produced to express modified MENA isoform variants with the candidate residues changed to amino acids that cannot be phosphorylated. In one example, serine was substituted with alanine, which has a similar R-group but lacks the hydroxyl group necessary for phosphoryl transfer. In other examples, tyrosine may be substituted with phenylalanine. Threonine may be substituted with either alanine or asparagine to block phosphorylation. Materials and methods for generating such mutants are well known to those of skill in the art (see for example, the Gene Art™ Site Directed Mutagenesis System (Life Technologies Corp., Grand Island, N.Y.), the Q5® Sire-Directed Mutagenesis Kit (New England Biolabs Inc., Beverly, Mass.), and the Quick-changes Site-Directed Mutagenesis Kit (Strata gene, La Jolla, Calif.)), The ability of tumor cell extracts to phosphorylate the modified MENA$^{INV}$ and MENA$^{11a}$ variant proteins was examined. Variants with significantly reduced levels of phosphorylation represent the amino acid target(s) for phosphorylation by tumor cell kinase(s). Such tumor cell kinases may be considered MENA isoform kinases.

Anti-phospho-MENA antibodies specific for the Ser125/Ser144 phosphorylation site in MENA/MENA$^{INV}$ were produced in animals injected with peptide containing mouse MENA residues 117-133 phosphorylated at Ser125 and conjugated to KLH (Covance Research Products, Denver, Pa.). Purification of pSer125MENA antibody was performed according to the protocol of Archuleta, et al. (Archuleta, Stutzke, Nixon, & Browning, Optimized protocol to make phospho-specific antibodies that work. Methods Mol. Biol. 717:69-88, 2011). Peptides used for purification (phosphorylated peptide: Ac-CKKGPTLPRQN(pS)QLPAQVQN (SEQ ID NO: 32) and dephosphorylated: CKKGPTLPRQNSQLPAQVAN (SEQ ID NO:32)) were prepared by Covance Research Products (BioLegend, San Diego, Calif.) and ThermoScientific, Grand Island, N.Y., respectively. Peptides were coupled to SulfoLink Coupling Resin Column (ThermoScientific) according to manufacturer's instructions. Sera were sequentially passed over column containing dephosphorylated peptide, and then over the column containing phosphorylated peptide. Antibodies bound to second column were eluted using IgG Elution buffer (ThermoScientific).

Phosphorylation of MENA and or MENA isoforms is inhibited by MENA kinase inhibitors from the Ras-Raf-MEK-MAPK/ERK and PI3K-AKT/mTOR pathways. The ATP-competitive MAPKAPK2/MK2 inhibitor PF-3644022 ((10R)-9,10,11,12-tetrahydro-10-methyl-3-(6-methyl-3-pyridinyl)-8H-[1,4]diazepino[5',6':4,5]thieno[3,2-f]quinolin-8-one hydrate) (TOCRIS, Bristol, UK), the non ATP-competitive MAPKAPK2/MK2 Hayess and Benndorf HSP25 peptide kinase inhibitor (KKKALNRQLGVAA (SEQ ID NO.: 30)) (Abcam, Cambridge, UK), p38 MAPK kinase inhibitor LY2228820 (5-[2-tert-butyl-4-(4-fluorophenyl)-1H-imidazol-5-yl]-3-(2,2-dimethylpropyl)imidazo[4,5-b]pyridin-2-amine; methanesulfonic acid) (Selleckchem, Houston Tex.), MEK1/MEK2 non ATP-competitive inhibitor PD0325901 (N-[(2R)-2,3-dihydroxypropoxy]-3,4-difluoro-2-[(2-fluoro-4-iodophenyl)amino]-benzamide) (Selleckchem, Houston Tex.), and Pi3K inhibitor LY294002 (2-morpholin-4-yl-8-phenylchromen-4-one) (Selleckchem, Houston Tex.) were each evaluated in vitro for the ability to block MENA kinase-dependent phosphorylation of Ser125 and Ser144 of MENA and MENA$^{INV}$ respectively, in mutant MVD7 and MDA-MB-231 cell lines. Phosphorylation was measured by quantitative immunoblot assays using MENA antibodies specific for the phosphorylation of MENA/MENA$^{INV}$ at Ser125/Ser144 Cells were stimulated and the MENA kinase was activated through treatment with 10 ng/ml TNF-alpha. Under these conditions MENA undergoes MENA kinase-dependent phosphorylation at Ser125 and MENA$^{INV}$ undergoes MENA kinase-dependent phosphorylation at Ser144. Commercially available phospho-specific HSP27 antibody (CellSignalling, Danvers, Mass.) was used to monitor MENA kinase-dependent phosphorylation of HSP27 as an internal control.

Figure 2:
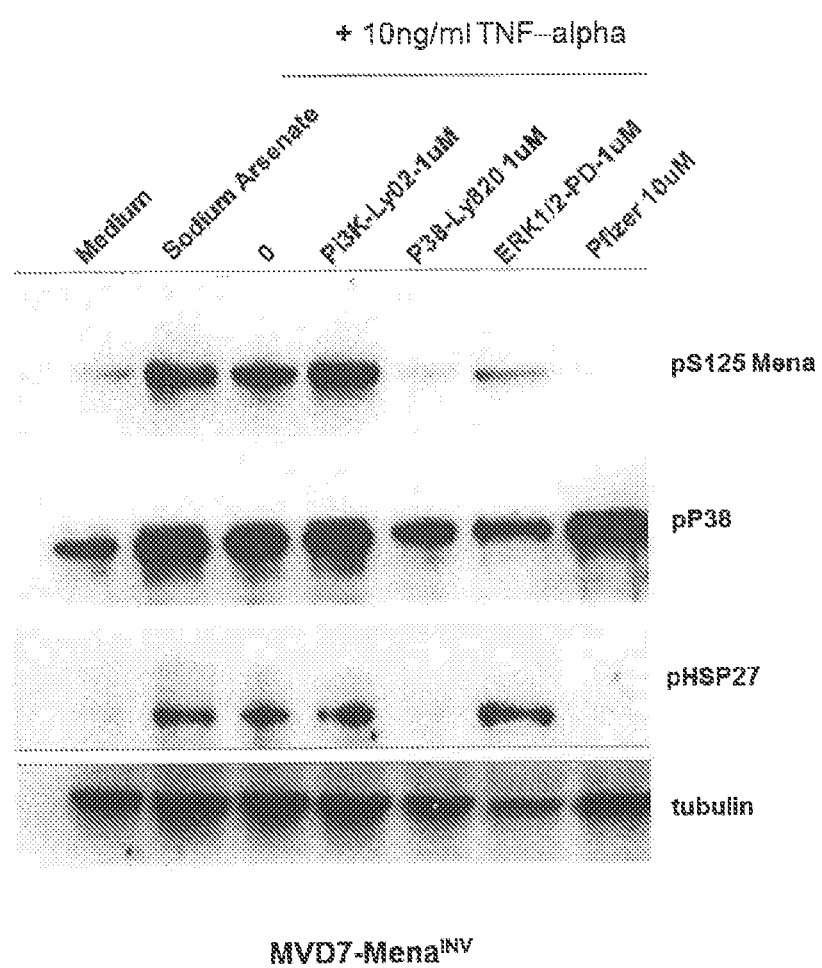
FIG. 2 presents Western blots of protein recovered from recombinant cell line MVD7-MENA$^{INV}$ probed with antibodies specific for presence of phosphorylated MENA at Scr125 (pSer125 MENA), phosphorylated P38 (pP38), phosphorylated HSP27 (pHSP27), and tubulin. Experimental samples were stimulated with TNF-alpha and treated with inhibitors, as indicated.

As shown in FIG. 2, the pSer125-specific antibody clearly differentiates between unphosphorylated MENA/MENA$^{INV}$ and phosphorylated MENA/MENA$^{INV}$, Comparison of the extent of antibody binding in the lane labeled "Medium" and the lane labeled "Sodium Arsenate" shows in the recombinant mouse embryonic fibroblast MVD7 cell line engineered to express MENA$^{INV}$ (MVD7-MENA$^{INV}$), the pSer125 MENA antibody produces very little signal in protein from cells that have minimal phosphorylation of MENA$^{INV}$ ("Medium"). The same cells when treated with sodium arsenate (osmotic stress inducer) to chemically modify the phosphorylatable sites of MENA$^{INV}$, produce a distinct signal when probed with the pSer125 MENA antibody. The Ser144 position of MENA$^{INV}$ is equivalent to Ser125 of MENA, with the difference in position solely due to the presence of the INV exon in MENA$^{INV}$. The pSer125 MENA antibody binds the Ser144 position of MENA$^{INV}$ as well as it binds the Ser125 position of MENA. Furthermore, comparison of the unstimulated and untreated (Medium) with the stimulated untreated (0) sample in FIG. 2 indicates stimulation of cells with TNF-alpha also elevates phosphorylation of MENA$^{INV}$. Shown in FIG. 2, treatment of stimulated cells with the p38 MAPK kinase inhibitor LY2228820 (at 1 uM, lane "P38-Ly820 1 uM")), MAPKAPK2/MK2 kinase inhibitor PF-3644022 (at 10 uM, lane "Pfizer 10 uM")), and MEK1/MEK2 inhibitor PD0325901 (at 1 uM, lane "ERK1/2-PD-1 uM")) significantly reduce the level of phosphorylated MENA$^{INV}$.

Figure 3:
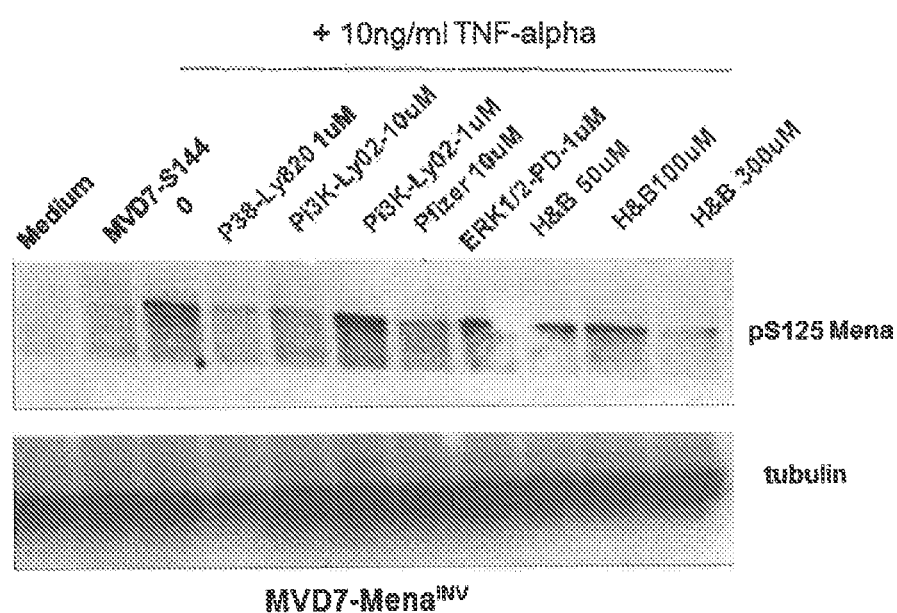
FIG. 3 presents Western blots of protein recovered from recombinant cell line of MVD7-MENA$^{INV}$ probed with antibodies to phosphorylated Ser125 of MENA (pSer125 MENA) and tubulin. Experimental samples were stimulated with TNF-alpha and treated with inhibitors as indicated.
Figure 4:
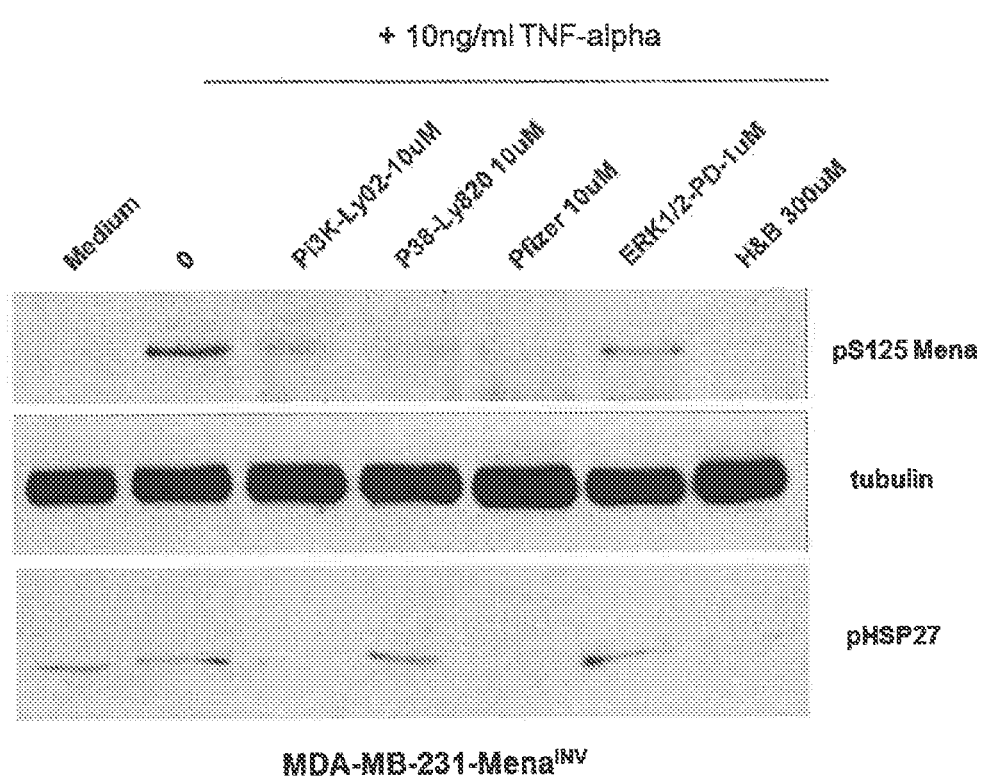
FIG. 4 represents Western blots of protein recovered from recombinant cell line of MDA-MB-231 MENA$^{INV}$ probed with antibodies to phosphorylated Ser125 of MENA (pSer125 MENA), tubulin, and phosphorylated HSP27 (pHSP27). Experimental samples were stimulated with TNF-alpha and treated with inhibitors as indicated.

FIG. 3 confirms this observation and extends the panel of inhibitors of FIG. 2 to include Pi3K kinase inhibitor LY294002 (at 1 and 10 uM, lanes "P38-Ly820 1 uM" and "P38-Ly820 1 uM", respectively) and the MAPKAPK2/MK2 kinase inhibitor KKKALHRQLGVAA (SEQ ID NO: 30) peptide at 50, 100, and 300 uM, lanes labeled "H&B" at the indicated inhibitor concentration. As shown in FIG. 4, human breast cancer MDA-MB-231 cells engineered to express MENA$^{INV}$ (MDA-MB-123-MENA$^{INV}$) clearly express elevated levels of phosphorylated Ser144, which can be detected using the antibody described above and as shown in lanes containing protein from cells unstimulated and untreated (0). Lanes labeled "P13K-Ly02-10 uM" are protein from stimulated cells treated with 10 uM of p38 MAPK kinase inhibitor LY2228820. Lanes labeled "P13K-Ly02-10 uM" and "P13K-Ly02-1 uM" contain protein from stimulated cells treated with 10 uM and 1 uM of Pi3K kinase inhibitor LY294002, respectively. Lanes labeled "Pfizer 10 uM" contain protein from stimulated cells treated with 10 uM of MAPKAPK2/MK2 kinase inhibitor PF-3644022. Lanes labeled ERK1/2-PD-1 uM contain protein from stimulated cells treated with 1 uM of MEK1/MEK2 inhibitor PD0325901, and lanes labeled "H&B" contain protein from stimulated cells treated with MAPKAPK2/MK2 kinase inhibitor KKKALHRQLGVAA (SEQ ID NO: 30) peptide at the indicated concentrations.

MENA kinase inhibitors limit cell spreading of MENA isoform recombinant cell lines. The ability of the various MENA kinase inhibitors described above to limit cell spreading of a MENA$^{INV}$ recombinant MVD7 (MVD7-MENA$^{INV}$) cell line was evaluated using a cell spreading assay. The assay involved pretreatment of the cell line with or without MENA kinase inhibitor at the concentrations indicated in FIG. 5 for 1 hour. Following pretreatment, the MVD7-MENA$^{INV}$ cells were allowed to attach and spread on fibronectin for 20 minutes. After 20 minutes the cells were fixed, permeabilized and stained with Phalloidin to visualize actin filaments. Images were acquired using imageJ software and analyzed (anova, n=5). Treatment groups were compared to control MVD7-GFP cells and plotted as Mean with S.E.M. as shown in FIG. 6.

Figure 5:
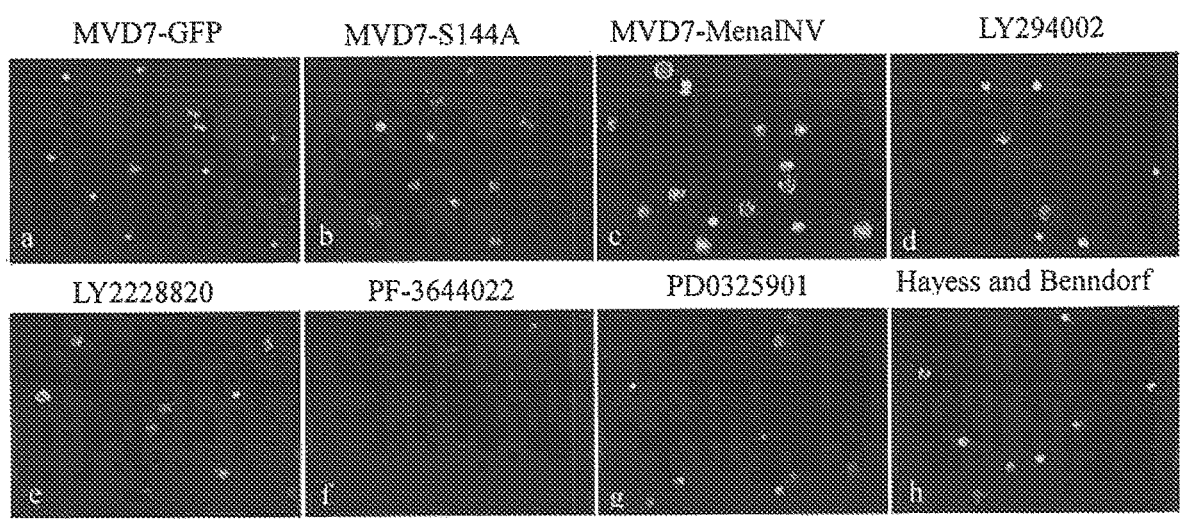
FIG. 5 is a collection of photomicrographs of cell spreading assays of various recombinant MVD7 cell lines treated with various inhibitors. Panel (a) MENA-null GFP control, panel (b) GFP-MENA (Ser144A), panel (c) untreated MVD7-MENA$^{INV}$, panel (d) MVD7-MENA$^{INV}$ treated with Pi3K kinase inhibitor LY294002 (PI3K-Ly02) 10 uM, panel (e) MVD7-MENA$^{INV}$ treated with p38 MAPK kinase inhibitor (LY2228820) 10 uM, panel (f) MVD7-MENA$^{INV}$ treated with MAPKAPK2/MK2 (PF-3644022) 10 uM, panel (g) MVD7-MENA$^{INV}$ treated with MEK1/MEK2 inhibitor (PD0325901) 1 uM, panel (h) MVD7-MENA$^{INV}$ treated with MAPKAPK2/MK2 kinase inhibitor KKKALHRQLGVAA (SEQ ID NO: 30) peptide (100 uM).
Figure 6:
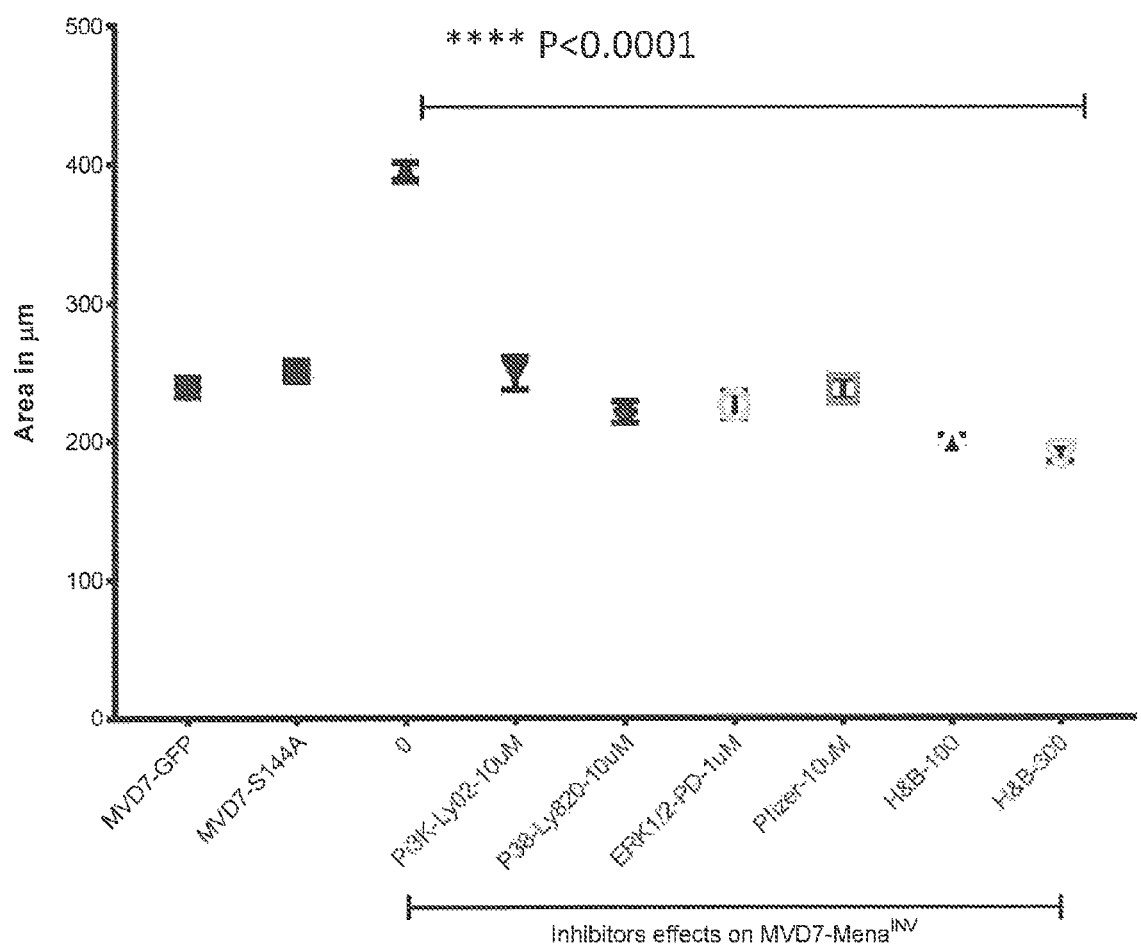
FIG. 6 is a plot of the results of the cell spreading assays of FIG. 5, where MVD7-GFP corresponds to panel (a), MVD-Ser144A corresponds to panel (b), 0 corresponds to panel (c), Pi3K kinase inhibitor LY294002 (PI3K-Ly02) 10 uM corresponds to panel (d), p38 MAPK kinase inhibitor (P38-Ly820) 10 uM corresponds to panel (e), MEK1/MEK2 kinase inhibitor (ERK12-PD) 1 uM corresponds to panel (f), MAPKAPK2/MK2 kinase inhibitor Pfizer PF-3644022 10 uM corresponds to panel (g), and H&B-100 denotes KKKA-LHRQLGVAA (SEQ ID NO: 30) peptide inhibitor at 100 uM corresponds to panel (h). H&B-300 denotes KKKA-LHRQLGVAA (SEQ ID NO: 30) peptide inhibitor at 300 uM (not shown in FIG. 5).

The MVD7-MENA$^{INV}$ cell shown in FIG. 5 panel (c) exhibited the MENA dependent spreading and adhesion phenotype which was not observed for the MVD7-GFP MENA-null control nor for the non-phosphorylatable MVD7-MENA$^{INV}$ (Ser144A) cells (FIG. 5, panels (a) and (b), respectively). Statistically significant reductions in the MENA-dependent spreading and adhesion phenotype were observed following incubation with the MENA kinase inhibitors at the indicated concentrations (FIG. 6). Statistically significant decreases in the MENA-dependent spreading and adhesion phenotype occurred with all MENA kinase inhibitors (FIG. 6). There were no statistically significant differences in spreading and adhesion between the MENA-null and MENA Ser125A non phosphorylatable mutant negative controls (FIG. 6.).

MENA kinase inhibitors reversed MENA-dependent fibrillogenesis. The ability of the various MENA kinase inhibitors described above to reverse MENA-dependent fibrillogenesis was evaluated in fibronectin fibrillogenesis assays using the MVD7-MENA$^{INV}$ cell line. Cells were pretreated with MENA kinase inhibitor for 1 hour at the concentrations indicated in FIG. 8 and cultured in medium containing fibronectin-depleted serum supplemented with labeled fibronectin. After 4 hours, fibronectin fibril formation was evaluated by quantitative immunostaining using imageJ software to measure abundance and distribution of fibrillar fibronectin (anova, n=3). The results are plotted relative to control MVD7-GFP cells in FIG. 8.

Figure 7:
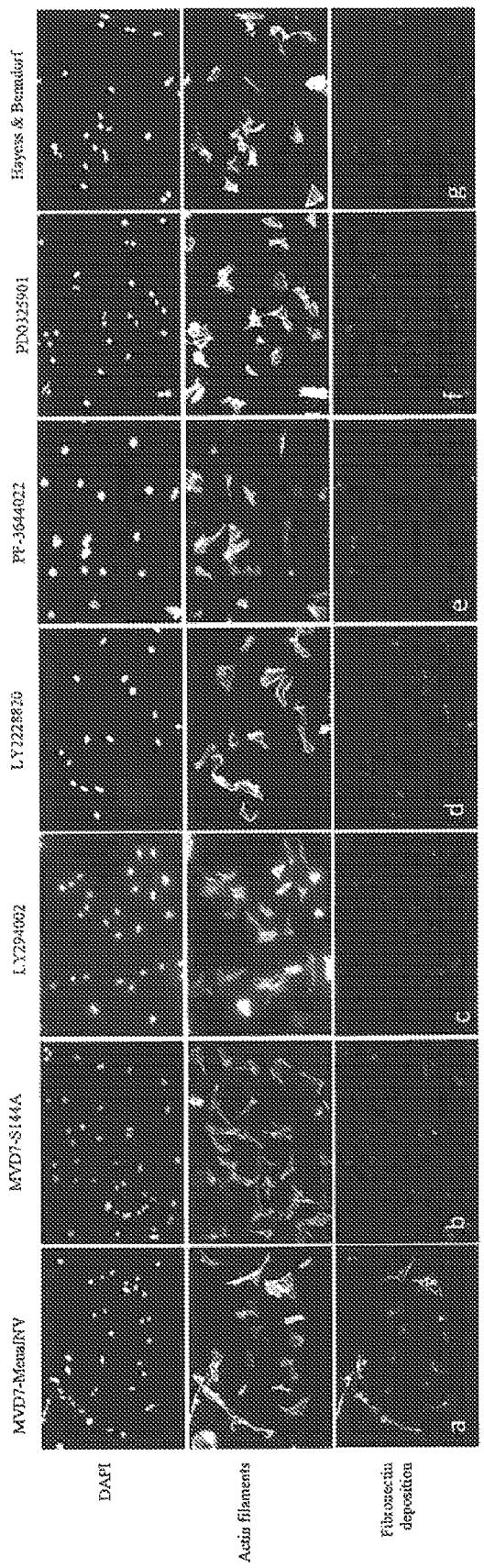
FIG. 7 is a collection of photomicrographs of fibronectin fibrillogenesis assays of the recombinant MVD7-MENA$^{INV}$ cell line (except as indicated in panels (a) and (b)) treated with various inhibitors and stained for DNA (DAPI) and for actin filaments (phalloidin) as well as fibronectin deposition. Panel (a) MVD7-GFP, panel (b) MVD7-MENA$^{INV}$ (Ser144A), panel (c) Pi3K kinase inhibitor (LY294002) 10 uM, panel (d) p38 MAPK kinase inhibitor (LY2228820) 10 uM, panel (e) MAPKAPK2/MK2 (PF-3644022) 10 uM, panel (f) MEK1/MEK2 inhibitor (PD0325901) 1 uM, and panels (g) MAPKAPK2/MK2 kinase inhibitor KKKA-LHRQLGVAA (SEQ ID NO: 30) peptide 100 and 300 uM, respectively.
Figure 8:
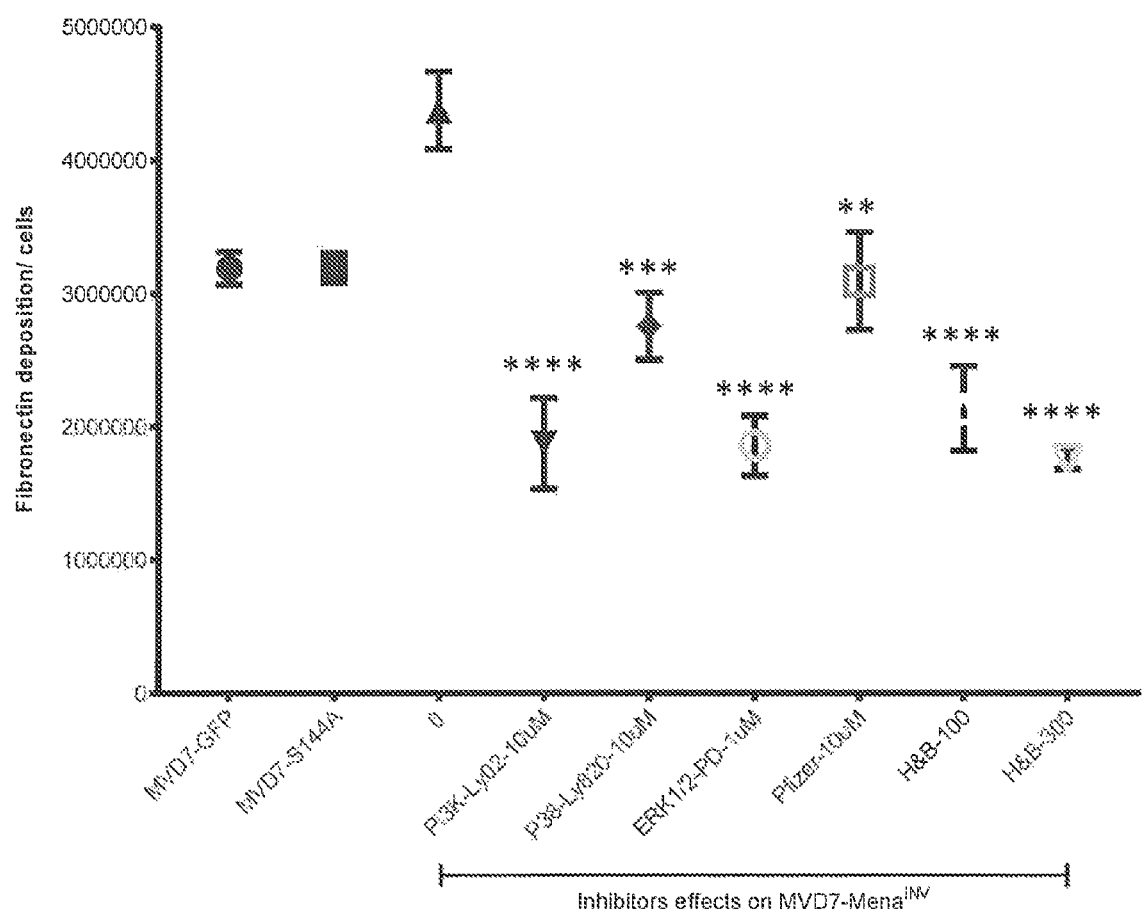
FIG. 8 is a plot of the results of the fibronectin fibrillogenesis assays (relative fibronectin deposition) of FIG. 7, where MVD7-GFP corresponds to panel (a), MVD7-Ser144A corresponds to panel (b), 0 represents fibronectin deposited by untreated MVD7-MENA$^{INV}$ cells, Pi3K kinase inhibitor LY294002 (PI3K-Ly02) 10 uM corresponds to panel (c), p38 kinase inhibitor LY2228820 (P38-Ly820) 10 uM corresponds to panel (d), MEK1/MEK2 inhibitor PD0325901 (ERK1/2-PD) 1 uM corresponds to panel (e), MAPKAPK2/MK2 kinase inhibitor (PF-3644022) 10 uM corresponds to panel (f), MAPKAPK2/MK2 kinase inhibitor KKKALHRQLGVAA (SEQ ID NO: 30) peptide (H&B-100) 100 uM corresponds to panel (g), and MAPKAPK2/MK2 kinase inhibitor KKKALHRQLGVAA (SEQ ID NO: 30) peptide (H&B-300) 300 uM corresponds to panel (h). Confidence levels are indicated by  for P=0.0022, * for P=0.0002, and **** for P<0.0001.

Untreated MVD7-MENA$^{INV}$v cells assemble a significant amount of fibronectin in fibrils (FIG. 7, panel (a). However, MVD7-GFP cells and the non-phosphorylatable mutant MENA$^{INV}$ (Ser144A) (FIG. 8 and FIG. 7 panel (b), respectively) fail to assemble a significant amount of fibronectin. Dose-dependent reductions in the MENA-dependent fibronectin fibrillogenesis phenotype were observed with increasing concentrations of the MAPKAPK2/MK2 kinase inhibitor KKKALHRQLGVAA (SEQ ID NO: 30) peptide at the concentrations of 100 and 300 uM (FIG. 7, panel (g) and FIG. 8). Statistically significant decreases in the MENA-dependent fibronectin fibrillogenesis phenotype was observed for all the Mena kinase inhibitors tested. Pi3K kinase inhibitor LY294002, MEK1/MEK2 kinase inhibitor PD0325901, and MAPKAPK2/MK2 kinase inhibitor KKKALHRQLGVAA (SEQ ID NO: 30) significantly reduced the MENA-dependent fibronectin fibrillogenesis phenotype compared to the MENA-null control (FIG. 8). There were no statistically significant differences in fibronectin deposition between the MENA-null negative control and MENA Ser144A non phosphorylatable mutant.

MENA kinase inhibitors block MENA-dependent cell migration in a wound-healing assay. The ability of the various MENA kinase inhibitors described above to block MENA-dependent cell migration of MDA-MB-231-MENA$^{INV}$ cells was assayed using the CySelect™ wound healing assay kit (Cell Biolabs, Inc., San Diego, Calif.). Following the manufacturer's protocol, cells were cultured in fibronectin coated wells until a monolayer formed around the wound insert. The insert was then removed and cells were cultured in the presence of inhibitor at the indicated concentrations in FIG. 9 in fully supplemented medium. After 18 hours the cells were fixed, stained, and evaluated for their capacity to close the wound generated by the insert by fluorescence microscopy.

Figure 9:
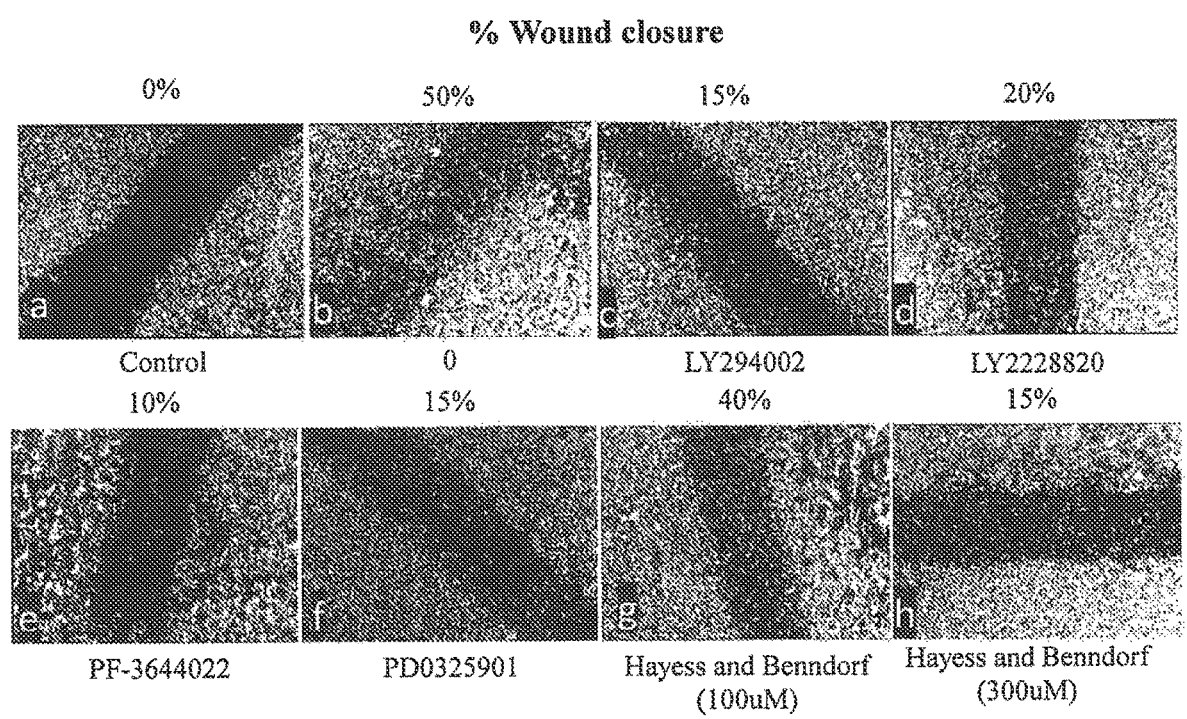
FIG. 9 is a collection of photomicrographs of cell migration in wound assays of MDA-MB-231-MEAN$^{INV}$ cells treated with various inhibitors. Estimated percentage of wound closure is presented above each panel. Panel (a) is cells before treatment, panel (b) cells after 18 hours in media without inhibitor, panel (c) cells after 18 hours in media supplemented with Pi3K kinase inhibitor LY294002 (10 uM), panel (d) cells after 18 hours in media supplemented with p38 kinase inhibitor LY2228820 (10 uM), panel (e) cells after 18 hours in media supplemented with MAPKAPK2/MK2 kinase inhibitor PF-3644022 (10 uM), panel (f) cells after 18 hours in media supplemented with MEK1/MEK2 kinase inhibitor PD0325901 (1 uM), panels (g) cells after 18 hours in media supplemented with MAPKAPK2/MK2 kinase inhibitor KKKALHRQLGVAA (SEQ ID NO: 30) peptide (H&B-100) 100 uM and h) cells after 18 hours in media supplemented with MAPKAPK2/MK2 kinase inhibitor KKKALHRQLGVAA (SEQ ID NO: 30) peptide (H&B-100) 300 uM.

As shown in FIG. 9, MDA-MB-231-MENA$^{INV}$ cells exhibit the MENA-dependent invasion phenotype in fully supplemented medium (panel (b)). Addition of MENA kinase inhibitors to cells grown in fully supplemented medium reduce the capability of the breast cancer cell line to migrate in the wound healing assay (panels (c)-(h)). Panel (a) represents the wound size at the start of treatment. Cells that were cultured overnight in fully supplemented medium without drug (panel (b)) were able to close 50% of the wound. Addition of the Pi3K kinase inhibitor LY294002 (10 uM) resulted in wound closure of only 15% (panel (c)), p38 MARK kinase inhibitor LY2228820 (10 uM) produced closure of only 20% (panel (d)), MAPKAPK2/MK2 kinase inhibitor PF-3644022 (10 uM) reduced wound closure to 10% (panel (e)), MEK1/MEK2 kinase inhibitor PD0325901 (1 uM) reduced wound closure to 15% (panel (f)), and the MAPKAPK2/MK2 kinase inhibitor KKKALHRQLGVAA (SEQ ID NO: 30) reduced wound closure to 15% of the wound when used at 300 uM (panel (h)). MENA kinase inhibitors inhibit MENA-dependent cell invasion and chemotaxis. The ability of the various MENA kinase inhibitors described above to inhibit MDA-MB-123-MENA$^{INV}$ tumor cell invasion was tested using the BioCoat™ Matrigel® invasion chamber assay (Corning, Tewksbury, Mass.). Following the manufacturer's protocol, MDA-MB-123-MENA$^{INV}$ cells were pretreated for 1 hour with inhibitor at the concentrations indicated in FIG. 10, then seeded above the layer of matrigel matrix membrane inserts. Inserts were transferred to wells containing basal media (negative control) and the chemoattractant EGF with or without each of the MENA kinase inhibitors. After 18 hours cells that invaded the lower cell surface of the membrane were fixed, stained and evaluated by quantitative immunostaining using imageJ software. Data were analyzed using anova, n=3 and reported relative to the negative control EGF stimulated cells in the absence of MENA kinase inhibitors (0) and plotted as the mean and standard error of the mean in FIG. 10.

Figure 10:
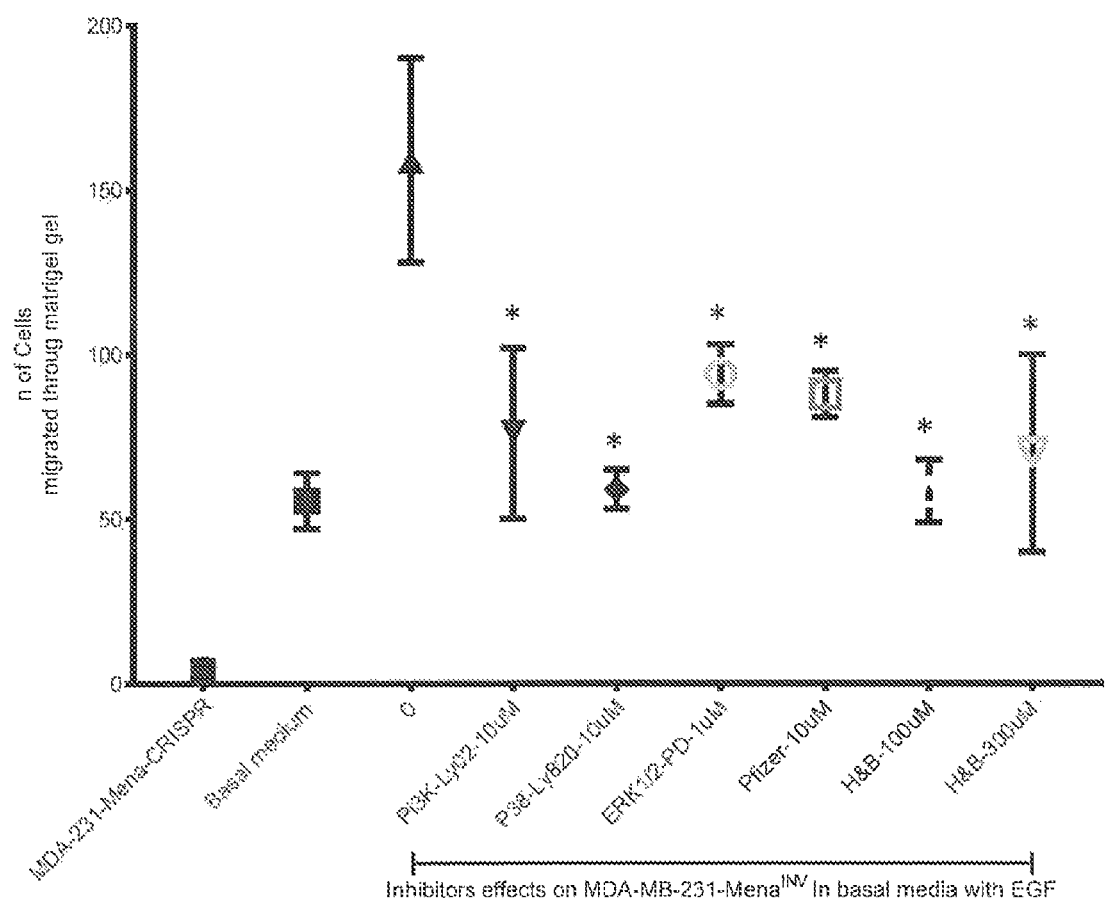
FIG. 10 is a plot of the results of the cell invasion and chemotaxis Matrigel assay. MENA kinase inhibitors reversed the MENA-dependent invasion and chemotaxis phenotype in MDA-MD-231-MENA$^{INV}$ tumor cells following incubation with Pi3K kinase LY294002 10 uM, p38 kinase inhibitor LY2228820 (P38-Ly820) 10 uM, MAPKAPK2/MK2 kinase inhibitor (PF-3644022) 10 uM, MEK1 and MEK2 inhibitor PD0325901 (ERK1/2-PD) 1 uM, and KKKALHRQLGVAA (SEQ ID NO: 30) peptide inhibitor 100 and 300 uM. MDA-MB-231-ΔMENA CRISPR mena-null cell line did not show any significant cell invasion and chemotaxis phenotype with few cells observed to migrate towards EGF. Confidence levels are indicated by * for P<0.04.

MDA-MB-231-MENA$^{INV}$ cells exhibit the invasive and chemotactic phenotype in basal medium containing EGF, compared to the MDA-MB-231-ΔMENA cell line, in which all endogenous MENA expression is deleted from the cell line using CRISPR-based techniques (FIG. 10). The addition of MENA kinase inhibitors significantly reduce the relative number of MDA-MB-231-MENA$^{INV}$ cells that invade through Matrigel insert membranes towards the EGF chemoattractant. The effect of incubation with the Pi3K kinase inhibitor LY294002 (10 uM) (P<0.028), p38 MARK kinase inhibitor LY2228820 (10 uM) (P<0.019), MAPKAPK2/MK2 kinase inhibitor PF-3644022 (10 uM) (P<0.040), MEK1/MEK2 PD0325901 (1 uM) (P<0.040) and MAPKAPK2/MK2 kinase inhibitor KKKALHRQLGVAA (SEQ ID NO: 30) (100 and 300 uM) (P<0.019 and P<0.020, respectively) are shown in FIG. 10. MENA kinase inhibitors significantly reversed the MENA-dependent invasion phenotype in MDA-MB-231-MENA$^{INV}$ cells to levels similar to the negative control, MDA-MB-23 I-MENA$^{INV}$ treated with basal medium only (Basal Medium).

MENA kinase inhibitors reverse MENA-dependent cell migration and chemotaxis in the Boyden Chamber Assay. MDA-MB-123-MENA$^{INV}$ tumor cells were pretreated with the MENA kinase inhibitors described above for 1 hour and loaded into the fibronectin coated 8 um pore polycarbonate membrane insert of the Boyden Chamber (Cell Biolabs, Inc.). The fibronectin coated upper chamber were then transferred to wells containing basal media (negative controls) and wells containing basal media, EGF, and MENA kinase inhibitors at the concentrations indicated in FIG. 11. All treatment conditions except the basal negative control used EGF as the chemoattractant. After 18 hours, cells that migrated through the pores toward the chemotattractant were evaluated by quantitative immunostaining using imageJ software as described above. Data were analyzed using anova (n=2) and reported relative to the EGF stimulated cells absent any inhibitor positive control (0) as mean with error of the mean in FIG. 11.

Figure 11:
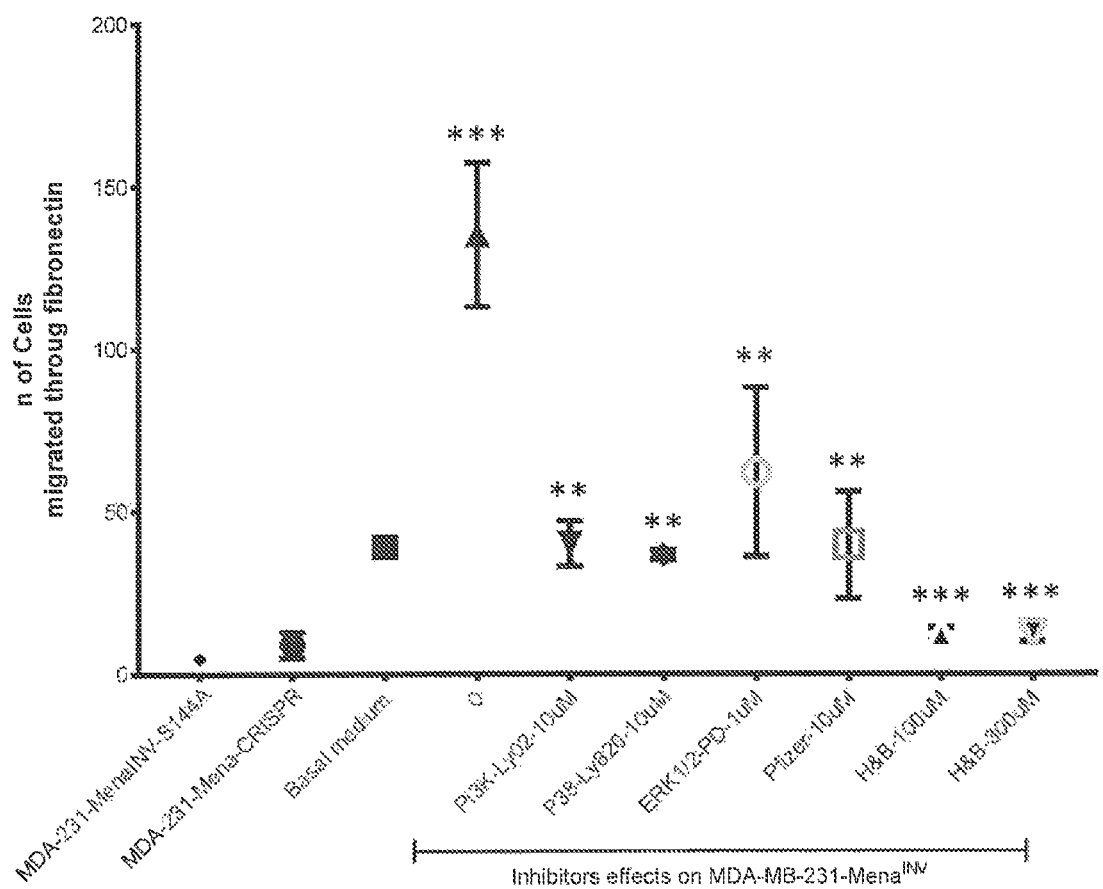
FIG. 11 is a plot of the result of cell migration and chemotaxis within the Boyden Chamber assay. MENA kinase inhibitors reversed the MENA-dependent migration and chemotaxis phenotype in MDA-MD-231MENA$^{INV}$ tumor cells following incubation with Pi3K kinase inhibitor LY294002 (PI3K-Ly02) 10 uM, p38 MAPK kinase inhibitor (LY2228820) 10 uM, MAPKAPK2/MK2 (PF-3644022) 10 uM, MEK1/MEK2 inhibitor PD0325901 (ERK1/2-PD) 1 uM and MAPKAPK2/MK2 kinase inhibitor KKKA-LHRQLGVAA (SEQ ID NO: 30) peptide 100 uM and 300 uM. Neither MDA-MB-231-ΔMENA CRISPR mena-null nor the non-phosphorylatable MENA-Ser144A cell lines exhibited the cell invasion and chemotaxis phenotype with few cells observed to migrate towards EGF. Confidence levels are indicated by  for P<0.04 and * for P<0.0004.

MDA-MB-231-MENA$^{INV}$ cells demonstrate the migration and chemotaxis MENA dependent-phenotype in basal medium containing EGF. This phenotype was not observed in MDA-MB-231-ΔMENA and non-phosphorylatable MENA-Ser144A cell lines using similar experimental conditions (FIG. 11). The addition of MENA kinase inhibitors significantly reduced the relative number of MDA-MB-231-MENA$^{INV}$ cells that migrated through the fibronectin coated insert membrane towards the EGF chemoattractant. Incubation with Pi3K kinase inhibitor LY294002 (10 uM) (P<0.028), p38 MARK kinase inhibitor LY2228820 (10 uM) (P<0.0018), MAPKAPK2/MK2 kinase inhibitor PF-3644022 (10 uM) (P<0.0018), MEK1/MEK2 kinase inhibitor PD0325901 (1 uM) (P<0.0031) and MAPKAPK2/MK2 kinase inhibitor KKKALHRQLGVAA (SEQ ID NO: 30) 100 and 300 uM (P<0.0004), (P<0.0004) significantly reverse the MENA-dependent invasion phenotype in MDA-MB-231-MENA$^{INV}$ cells to levels similar to the negative control, MDA-MB-231-MENA$^{INV}$ treated with basal medium only.

Example 2

Identifying Small Molecule MENA Isoform Kinase Inhibitors

Small molecule MENA isoform kinase inhibitors are identified by use of the same (or similar) panel of in vitro assays as described in Example 1. To identify small molecule inhibitors of MENA kinases, single molecules, or pools of molecules, from commercial combinatorial chemical libraries of compounds based on known protein kinase inhibitor structures (scaffolds), such as aminocyoanopyridine, pyrazolopyrimidines, pyrrolopyridine, carboline, pyrrolopyrimidone, and CMPD 1 are assayed for their ability to reduce phosphorylation of the respective MENA isoform substrates using the assays described above. Such methods are well known to those in the art (reviewed by von Ohsen and Bomer, 2005, Wang and Ma, 2015). Libraries of potential kinase inhibitors are commercially available (cf. SYNkinase, Parkville, Victoria, Australia) and screening can be carried out under commercial service (e.g. the KiNativ™ service described in Patricelli, et al., 2011. Inhibitors identified in the assay may be modified by methods well known in the art to optimize their inhibitory characteristics and to improve drugability. Those exhibiting the most advantageous inhibitor profiles are selected for further in vivo testing as described below.

Example 3

Identifying MENA Isoform Kinase Peptide Inhibitors

Peptide MENA isoform kinase inhibitors are identified by use of the same (or similar) panel of in vitro assays as described in Example 1. Peptides comprising SEQ ID Nos.: 14-29 are assayed and those with the best inhibitor profiles selected for further in vivo testing as described in further examples herein.

Example 4

MENA Kinase Inhibitors Reduce Incidence of Metastatic Cancer in an In Vivo PyMT Mouse Model The ability of the MENA kinase inhibitors to reduce metastasis in the PyMT mouse breast cancer model (described in detail by Harney, et al., 2015) is assayed by administering an effective dose of the inhibitor to a mouse with a previously established xenograft tumor. Appropriate doses of the inhibitor may be determined by methods well known in the art. In these experiments, the baseline level of circulating tumor cells and tumor cell dissemination is established and the MENA kinase inhibitor is then administered to the mouse. Subsequent changes in MetaSites, circulating tumor cell numbers, and lung metastases are monitored. Reduction of levels of number of MetaSites, circulating tumor cells, and lung metastases indicate that the MENA kinase inhibitor reduces cancer metastasis in pre-existing metastatic tumors.

Additional experiments are carried out to determine efficacy of $MENA^{INV}$ kinase inhibitors to suppress tumor metastasis. These additional experiments involve treatment of the subject mouse with $MENA^{INV}$ kinase inhibitor prior to introduction of the xenograft tumor and determining Meta-Site density and the level of circulating tumor cells through the course of tumor development. Reduction in MetaSite density and tumor cell circulation relative to the baseline numbers established in matched untreated control mice indicates that the $MENA^{11a}$ kinase inhibitor effectively inhibits establishment of the metastatic phenotype.

Example 5

MENA Kinase Inhibitors Reduce Incidence of Metastatic Cancer in a Mouse Model

The ability of the MENA kinase inhibitors to reduce metastasis in a nod/skid mouse transplanted with a human triple negative breast cancer (TNBC) cell line MDA-MB-231 (described in detail by Odin et al., 2017) is determined. These experiments involve assessing organs upon sacrifice for the presence of metastatic lesions and blood for increase in the number of circulation tumor cells (CTC's). Reduction of levels of circulating tumor cells and lung metastases indicate that the MENA kinase inhibitor reduces cancer metastasis.

Example 6

Combination Treatment with MENA-Kinase Inhibitors and Paclitaxel Restores Paclitaxel Sensitivity and Reduces Paclitaxel-Induced Tumor Cell Dissemination Cytotoxic chemotherapy, including the use of taxanes, remains the standard of care for treatment of advanced cancer and aggressive cancer such as Triple Negative Breast Cancer (TNBC). Despite the benefits associated with cytotoxic chemotherapy response rates can be low and for example TNBC can become resistant within a year of treatment. Treatment with paclitaxel can also induce tumor cell dissemination. Taxanes such as paclitaxel cause mitotic catastrophe by stabilizing microtubules and inhibiting disassembly during metaphase leading to mitotic arrest and cell death. $MENA^{INV}$ expression alters the ratio of dynamic and stable microtubule populations in paclitaxel-treated tumor cells. MENA expression also increases MAPK signaling in response to paclitaxel treatment. Decreasing phosphorylation of $MENA^{INV}$ by co-treatment with MENA kinase inhibitors can restore paclitaxel sensitivity by driving microtubule stabilization.

Example 7

Combination Treatment with MENA Isoform Kinase Inhibitors and Gefitinib Reduces Spontaneous Resistance to Gefitinib The EGFR specific TKI, gefitinib, is effective in initial treatment of many cancers, particularly non-small-cell lung cancers, but frequently loses efficacy due to compensatory mutations within EGFR or in ancillary receptor pathways [reviewed in Kosaka, et al., 2011]. Other drugs suitable for use in the practice of present invention include but are not limited to: Erbitux® (Cetuximab), Tarceva® (Erlotinb), Iressa® (Gefitinb), Tykerb® (Lapatinib), Cometriq® (Cabozantinib), Xalkori® (Crizotinib), Vectibix® (Panitumumab), and Gioreif® (Afatinib). Drugs which are currently in development which are suitable for use in the practice of present invention include but are not limited to: tivantinib (ARQ97), rilotumumab (AMG 102), AMG479 (IGF-1R inhibitor), AMG 337 (c-MET inhibitor), ficlatuzumab (AV-299), tivantinib (ARQ197) and onartuzumab (c-MET inhibitor). MENA's role in recruiting the PTP1b kinase/dephosphorylase to EGFR [see Hughes, et al., 2015] suggests that the combined effect of modulating the phosphorylation of EGFR directly with gefitinib and indirectly via MENA may reduce the incidence of spontaneous resistance to gefitinib. To test the ability of MENA isoform kinase inhibitors to reduce the incidence of spontaneous resistance to gefitinib, gefitinib and MENA isoform kinase inhibitor are administered to PyMT mouse breast cancer model mice, individually and in combination after establishment of the xenograft tumor as described above. MetaSite density and the level of circulating tumor cells are monitored through the course of tumor development. Significant decreases in overall Meta-Site density and circulating tumor cells in the mice receiving both gefitinib and MENA isoform kinase inhibitor, relative to mice receiving gefitinib or the MENA isoform kinase inhibitor alone, indicate that the combination therapy is effective. The kinetics of MetaSite development and observed level of circulating tumor cells provides insight into the ability of the MENA isoform kinase inhibitor to retard development of gefitinib resistance. Significant delays in developing significant MetaSite levels and increased circulating tumor cells in mice receiving the combination therapy relative to mice receiving just gefitinib indicate that the MENA isoform kinase inhibitors suppress development of gefitinib resistance.

What is claimed is:

1. A method for the treatment of a cancer or fibrotic disorder associated with elevated MENA protein (SEQ ID NO: 1) and/or MENA$^{INV}$ protein (SEQ ID NO: 3) in a subject in need thereof, comprising administering to the subject a therapeutically effective amount of a protein kinase inhibitor that inhibits phosphorylation of a serine residue on a MENA isoform substrate, selected from at least one of MENA protein (SEQ ID NO: 1) or MENA$^{INV}$ protein (SEQ ID NO: 3), wherein the protein kinase inhibitor inhibits the transfer of phosphate to Ser125 of SEQ ID NO:1 and/or inhibits the transfer of phosphate to Ser144 of SEQ ID NO:3 and wherein the protein kinase inhibitor inhibits a MAP kinase signaling pathway.

2. The method according to claim 1, wherein the protein kinase inhibitor is at least one of a MAPKAPK2/MK2 inhibitor, p38 MAPK inhibitor, and MEK inhibitor.

3. The method according to claim 2, wherein the protein kinase inhibitor is a MAPKAPK2/MK2 inhibitor.

4. The method according to claim 1, wherein the protein kinase inhibitor is administered to the subject orally, intravenously, intramuscularly, intraperitoneally, intrapulmonarily, intratumorally, intranasally, intrathecally or subcutaneously.

5. The method according to claim 1, wherein the protein kinase inhibitor is co-administered to the subject with another therapeutic agent.

6. The method according to claim 5, wherein the protein kinase inhibitor is co-administered to the subject with a tyrosine kinase inhibitor or an anti-microtubule agent.

7. The method according to claim 6, wherein the protein kinase inhibitor is administered to the subject prior to, in conjunction with, or subsequent to administration of the tyrosine kinase inhibitor or anti-microtubule agent.

8. The method according to claim 7, wherein the protein kinase inhibitor is co-administered to the subject with an anti-microtubule agent selected from docetaxel, paclitaxel, albumin-bound paclitaxel, and cabazitaxel.

9. The method according to claim 6, wherein the protein kinase inhibitor is co-administered to the subject with a tyrosine kinase inhibitor specific to the group of tyrosine kinase receptors selected from the group consisting of EGF receptor (EGFR), HER2/neu, c-SRC, hepatocyte growth factor receptor (HGFR), insulin-like growth factor 1 receptor, fibroblast growth factor receptor, platelet-derived growth factor receptor, and VEGF receptor; or gefitinib.

10. The method according to claim 1, wherein the disorder is cancer.

11. The method according to claim 10, wherein the cancer is selected from multiple myeloma, acute lymphocytic leukemia, acute and chronic myelogenous leukemia, chronic lymphocytic leukemia, acute lymphoblastic leukemia, promyelocytic leukemia, B-cell lymphoma, T-cell lymphoma, mantle cell lymphoma, hairy cell lymphoma, Burkiti's lymphoma, mast cell tumors, Hodgkin's disease, non-Hodgkin's disease, myelodysplasia syndrome, fibrosarcoma, rhabdomyosarcoma; astrocytoma, neuroblastoma, glioma, schwannomas, melanoma, seminoma, teratocarcinoma, osteosarcoma, xenodenna pigmentosum, keratoctanthoma, thyroid follicular cancer, Kaposi's sarcoma, melanoma, teratotna, rhabdomyosarcoma, metastatic and bone disorders, cancer of the bone, mouth/pharynx, esophagus, larynx, stomach, intestine, colon, rectum, lung, liver, pancreas, nerve, brain, head and neck, throat, ovary, uterus, prostate, testis, bladder, kidney, breast, gall bladder, cervix, thyroid, prostate, and skin, non-small cell lung cancer, small cell lung cancer, glioma, and glioblastoma multiforme.

12. The method according to claim 10, wherein the cancer is a metastatic cancer.

13. The method according to claim 12, wherein the cancer is a lung metastasis.

* * * * *

SEQUENCE LISTING

<160> NUMBER OF SEQ ID NOS: 32

<210> SEQ ID NO 1
<211> LENGTH: 570
<212> TYPE: PRT
<213> ORGANISM: Homo sapiens

<400> SEQUENCE: 1

Met Ser Glu Gln Ser Ile Cys Gln Ala Arg Ala Ala Val Met Val Tyr
1               5                   10                  15

Asp Asp Ala Asn Lys Lys Trp Val Pro Ala Gly Gly Ser Thr Gly Phe
            20                  25                  30

Ser Arg Val His Ile Tyr His His Thr Gly Asn Asn Thr Phe Arg Val
        35                  40                  45

Val Gly Arg Lys Ile Gln Asp His Gln Val Val Ile Asn Cys Ala Ile
    50                  55                  60

Pro Lys Gly Leu Lys Tyr Asn Gln Ala Thr Gln Thr Phe His Gln Trp
65                  70                  75                  80

Arg Asp Ala Arg Gln Val Tyr Gly Leu Asn Phe Gly Ser Lys Glu Asp
                85                  90                  95

Ala Asn Val Phe Ala Ser Ala Met Met His Ala Leu Glu Val Leu Asn
            100                 105                 110

Ser Gln Glu Thr Gly Pro Thr Leu Pro Arg Gln Asn Ser Gln Leu Pro
        115                 120                 125

Ala Gln Val Gln Asn Gly Pro Ser Gln Glu Glu Leu Glu Ile Gln Arg
    130                 135                 140

Arg Gln Leu Gln Glu Gln Arg Gln Lys Glu Leu Glu Arg Glu Arg
145                 150                 155                 160

Leu Glu Arg Glu Arg Met Glu Arg Glu Arg Leu Glu Arg Glu Arg Leu
                165                 170                 175

Glu Arg Glu Arg Leu Glu Arg Glu Arg Leu Glu Gln Glu Gln Leu Glu
            180                 185                 190

Arg Glu Arg Gln Glu Arg Glu Arg Gln Glu Arg Leu Glu Arg Gln Glu
        195                 200                 205

Arg Leu Glu Arg Gln Glu Arg Leu Glu Arg Gln Glu Arg Leu Asp Arg
    210                 215                 220

Glu Arg Gln Glu Arg Gln Glu Arg Glu Arg Leu Glu Arg Leu Glu Arg
225                 230                 235                 240

Glu Arg Gln Glu Arg Glu Arg Gln Glu Gln Leu Glu Arg Glu Gln Leu
                245                 250                 255

Glu Trp Glu Arg Glu Arg Arg Ile Ser Ser Ala Ala Ala Pro Ala Ser
            260                 265                 270

Val Glu Thr Pro Leu Asn Ser Val Leu Gly Asp Ser Ser Ala Ser Glu
        275                 280                 285

Pro Gly Leu Gln Ala Ala Ser Gln Pro Ala Glu Thr Pro Ser Gln Gln
    290                 295                 300

Gly Ile Val Leu Gly Pro Leu Ala Pro Pro Pro Pro Pro Leu Pro
305                 310                 315                 320

Pro Gly Pro Ala Gln Ala Ser Val Ala Leu Pro Pro Pro Pro Gly Pro
                325                 330                 335

Pro Pro Pro Pro Leu Pro Ser Thr Gly Pro Pro Pro Pro Pro Pro
            340                 345                 350

Pro Pro Pro Leu Pro Asn Gln Val Pro Pro Pro Pro Pro Pro
        355                 360                 365

```
Ala Pro Pro Leu Pro Ala Ser Gly Phe Phe Leu Ala Ser Met Ser Glu
        370             375                 380

Asp Asn Arg Pro Leu Thr Gly Leu Ala Ala Ile Ala Gly Ala Lys
385             390                 395                 400

Leu Arg Lys Val Ser Arg Met Glu Asp Thr Ser Phe Pro Ser Gly Gly
                405                 410                 415

Asn Ala Ile Gly Val Asn Ser Ala Ser Ser Lys Thr Asp Thr Gly Arg
            420                 425                 430

Gly Asn Gly Pro Leu Pro Leu Gly Gly Ser Gly Leu Met Glu Glu Met
        435                 440                 445

Ser Ala Leu Leu Ala Arg Arg Arg Ile Ala Glu Lys Gly Ser Thr
450                 455                 460

Ile Glu Thr Glu Gln Lys Glu Asp Lys Gly Glu Asp Ser Glu Pro Val
465             470                 475                 480

Thr Ser Lys Ala Ser Ser Thr Ser Thr Pro Glu Pro Thr Arg Lys Pro
                485                 490                 495

Trp Glu Arg Thr Asn Thr Met Asn Gly Ser Lys Ser Pro Val Ile Ser
                500                 505                 510

Arg Pro Lys Ser Thr Pro Leu Ser Gln Pro Ser Ala Asn Gly Val Gln
            515                 520                 525

Thr Glu Gly Leu Asp Tyr Asp Arg Leu Lys Gln Asp Ile Leu Asp Glu
530                 535                 540

Met Arg Lys Glu Leu Thr Lys Leu Lys Glu Glu Leu Ile Asp Ala Ile
545                 550                 555                 560

Arg Gln Glu Leu Ser Lys Ser Asn Thr Ala
                565                 570

<210> SEQ ID NO 2
<211> LENGTH: 19
<212> TYPE: PRT
<213> ORGANISM: Artificial Sequence
<220> FEATURE:
<223> OTHER INFORMATION: MenaINV exon sequence

<400> SEQUENCE: 2

Ala Gln Ser Lys Val Thr Ala Thr Gln Asp Ser Thr Asn Leu Arg Cys
1               5                   10                  15

Ile Phe Cys

<210> SEQ ID NO 3
<211> LENGTH: 589
<212> TYPE: PRT
<213> ORGANISM: Homo sapiens

<400> SEQUENCE: 3

Met Ser Glu Gln Ser Ile Cys Gln Ala Arg Ala Ala Val Met Val Tyr
1               5                   10                  15

Asp Asp Ala Asn Lys Lys Trp Val Pro Ala Gly Gly Ser Thr Gly Phe
            20                  25                  30

Ser Arg Val His Ile Tyr His His Thr Gly Asn Asn Thr Phe Arg Val
        35                  40                  45

Val Gly Arg Lys Ile Gln Asp His Gln Val Val Ile Asn Cys Ala Ile
    50                  55                  60

Pro Lys Gly Leu Lys Tyr Asn Gln Ala Thr Gln Thr Phe His Gln Trp
65                  70                  75                  80

Arg Asp Ala Arg Gln Val Tyr Gly Leu Asn Phe Gly Ser Lys Glu Asp
                85                  90                  95
```

```
Ala Asn Val Phe Ala Ser Ala Met Met His Ala Leu Glu Val Leu Asn
            100                 105                 110

Ser Gln Glu Thr Ala Gln Ser Lys Val Thr Ala Thr Gln Asp Ser Thr
            115                 120                 125

Asn Leu Arg Cys Ile Phe Cys Gly Pro Thr Leu Pro Arg Gln Asn Ser
            130                 135                 140

Gln Leu Pro Ala Gln Val Gln Asn Gly Pro Ser Gln Glu Glu Leu Glu
145                 150                 155                 160

Ile Gln Arg Arg Gln Leu Gln Glu Gln Arg Gln Lys Glu Leu Glu
                165                 170                 175

Arg Glu Arg Leu Glu Arg Glu Arg Met Glu Arg Glu Arg Leu Glu Arg
            180                 185                 190

Glu Arg Leu Glu Arg Glu Arg Leu Glu Arg Glu Arg Leu Glu Gln Glu
                195                 200                 205

Gln Leu Glu Arg Glu Arg Gln Glu Arg Glu Arg Gln Glu Arg Leu Glu
            210                 215                 220

Arg Gln Glu Arg Leu Glu Arg Gln Glu Arg Leu Glu Arg Gln Glu Arg
225                 230                 235                 240

Leu Asp Arg Glu Arg Gln Glu Arg Gln Glu Arg Glu Arg Leu Glu Arg
                245                 250                 255

Leu Glu Arg Glu Arg Gln Glu Arg Glu Arg Gln Glu Gln Leu Glu Arg
            260                 265                 270

Glu Gln Leu Glu Trp Glu Arg Glu Arg Arg Ile Ser Ser Ala Ala Ala
            275                 280                 285

Pro Ala Ser Val Glu Thr Pro Leu Asn Ser Val Leu Gly Asp Ser Ser
            290                 295                 300

Ala Ser Glu Pro Gly Leu Gln Ala Ala Ser Gln Pro Ala Glu Thr Pro
305                 310                 315                 320

Ser Gln Gln Gly Ile Val Leu Gly Pro Leu Ala Pro Pro Pro Pro Pro
                325                 330                 335

Pro Leu Pro Pro Gly Pro Ala Gln Ala Ser Val Ala Leu Pro Pro Pro
            340                 345                 350

Pro Gly Pro Pro Pro Pro Pro Leu Pro Ser Thr Gly Pro Pro Pro
            355                 360                 365

Pro Pro Pro Pro Pro Pro Leu Pro Asn Gln Val Pro Pro Pro Pro Pro
            370                 375                 380

Pro Pro Pro Ala Pro Pro Leu Pro Ala Ser Gly Phe Phe Leu Ala Ser
385                 390                 395                 400

Met Ser Glu Asp Asn Arg Pro Leu Thr Gly Leu Ala Ala Ala Ile Ala
                405                 410                 415

Gly Ala Lys Leu Arg Lys Val Ser Arg Met Glu Asp Thr Ser Phe Pro
            420                 425                 430

Ser Gly Gly Asn Ala Ile Gly Val Asn Ser Ala Ser Ser Lys Thr Asp
            435                 440                 445

Thr Gly Arg Gly Asn Gly Pro Leu Pro Leu Gly Gly Ser Gly Leu Met
            450                 455                 460

Glu Glu Met Ser Ala Leu Leu Ala Arg Arg Arg Arg Ile Ala Glu Lys
465                 470                 475                 480

Gly Ser Thr Ile Glu Thr Glu Gln Lys Glu Asp Lys Gly Glu Asp Ser
                485                 490                 495

Glu Pro Val Thr Ser Lys Ala Ser Ser Thr Ser Thr Pro Glu Pro Thr
            500                 505                 510
```

-continued

```
Arg Lys Pro Trp Glu Arg Thr Asn Thr Met Asn Gly Lys Ser Pro
            515                 520                 525

Val Ile Ser Arg Pro Lys Ser Thr Pro Leu Ser Gln Pro Ser Ala Asn
530                 535                 540

Gly Val Gln Thr Glu Gly Leu Asp Tyr Asp Arg Leu Lys Gln Asp Ile
545                 550                 555                 560

Leu Asp Glu Met Arg Lys Glu Leu Thr Lys Leu Lys Glu Glu Leu Ile
                565                 570                 575

Asp Ala Ile Arg Gln Glu Leu Ser Lys Ser Asn Thr Ala
            580                 585

<210> SEQ ID NO 4
<211> LENGTH: 21
<212> TYPE: PRT
<213> ORGANISM: Artificial Sequence
<220> FEATURE:
<223> OTHER INFORMATION: Mena11a Exon Sequence

<400> SEQUENCE: 4

Arg Asp Ser Pro Arg Lys Asn Gln Ile Val Phe Asp Asn Arg Ser Tyr
1               5                   10                  15

Asp Ser Leu His Arg
            20

<210> SEQ ID NO 5
<211> LENGTH: 591
<212> TYPE: PRT
<213> ORGANISM: Homo sapiens

<400> SEQUENCE: 5

Met Ser Glu Gln Ser Ile Cys Gln Ala Arg Ala Ala Val Met Val Tyr
1               5                   10                  15

Asp Asp Ala Asn Lys Lys Trp Val Pro Ala Gly Gly Ser Thr Gly Phe
            20                  25                  30

Ser Arg Val His Ile Tyr His His Thr Gly Asn Asn Thr Phe Arg Val
        35                  40                  45

Val Gly Arg Lys Ile Gln Asp His Gln Val Val Ile Asn Cys Ala Ile
    50                  55                  60

Pro Lys Gly Leu Lys Tyr Asn Gln Ala Thr Gln Thr Phe His Gln Trp
65                  70                  75                  80

Arg Asp Ala Arg Gln Val Tyr Gly Leu Asn Phe Gly Ser Lys Glu Asp
                85                  90                  95

Ala Asn Val Phe Ala Ser Ala Met Met His Ala Leu Glu Val Leu Asn
            100                 105                 110

Ser Gln Glu Thr Gly Pro Thr Leu Pro Arg Gln Asn Ser Gln Leu Pro
        115                 120                 125

Ala Gln Val Gln Asn Gly Pro Ser Gln Glu Glu Leu Glu Ile Gln Arg
    130                 135                 140

Arg Gln Leu Gln Glu Gln Gln Arg Gln Lys Glu Leu Glu Arg Glu Arg
145                 150                 155                 160

Leu Glu Arg Glu Arg Met Glu Arg Glu Arg Leu Glu Arg Glu Arg Leu
                165                 170                 175

Glu Arg Glu Arg Leu Glu Arg Glu Arg Leu Glu Gln Gln Leu Glu
            180                 185                 190

Arg Glu Arg Gln Glu Arg Glu Arg Gln Glu Leu Glu Arg Gln Glu
        195                 200                 205

Arg Leu Glu Arg Gln Glu Arg Leu Glu Arg Gln Glu Arg Leu Asp Arg
```

```
            210                 215                 220

Glu Arg Gln Glu Arg Gln Arg Glu Arg Leu Glu Arg Leu Glu Arg
225                 230                 235                 240

Glu Arg Gln Glu Arg Glu Arg Gln Gln Leu Glu Arg Glu Gln Leu
                245                 250                 255

Glu Trp Glu Arg Glu Arg Arg Ile Ser Ala Ala Ala Pro Ala Ser
            260                 265                 270

Val Glu Thr Pro Leu Asn Ser Val Leu Gly Asp Ser Ala Ser Glu
        275                 280                 285

Pro Gly Leu Gln Ala Ala Ser Gln Pro Ala Glu Thr Pro Ser Gln Gln
    290                 295                 300

Gly Ile Val Leu Gly Pro Leu Ala Pro Pro Pro Pro Pro Leu Pro
305                 310                 315                 320

Pro Gly Pro Ala Gln Ala Ser Val Ala Leu Pro Pro Pro Gly Pro
                325                 330                 335

Pro Pro Pro Pro Pro Leu Pro Ser Thr Gly Pro Pro Pro Pro Pro
            340                 345                 350

Pro Pro Pro Leu Pro Asn Gln Val Pro Pro Pro Pro Pro Pro Pro
        355                 360                 365

Ala Pro Pro Leu Pro Ala Ser Gly Phe Phe Leu Ala Ser Met Ser Glu
    370                 375                 380

Asp Asn Arg Pro Leu Thr Gly Leu Ala Ala Ala Ile Ala Gly Ala Lys
385                 390                 395                 400

Leu Arg Lys Val Ser Arg Met Glu Asp Thr Ser Phe Pro Ser Gly Gly
                405                 410                 415

Asn Ala Ile Gly Val Asn Ser Ala Ser Ser Lys Thr Asp Thr Gly Arg
            420                 425                 430

Gly Asn Gly Pro Leu Pro Leu Gly Gly Ser Gly Leu Met Glu Glu Met
        435                 440                 445

Ser Ala Leu Leu Ala Arg Arg Arg Ile Ala Glu Lys Gly Ser Thr
    450                 455                 460

Ile Glu Thr Glu Gln Lys Glu Asp Lys Gly Glu Asp Ser Glu Pro Val
465                 470                 475                 480

Thr Ser Lys Ala Ser Ser Thr Ser Thr Pro Glu Pro Thr Arg Lys Pro
                485                 490                 495

Trp Glu Arg Thr Asn Thr Met Asn Gly Ser Lys Ser Pro Val Ile Ser
            500                 505                 510

Arg Arg Asp Ser Pro Arg Lys Asn Gln Ile Val Phe Asp Asn Arg Ser
        515                 520                 525

Tyr Asp Ser Leu His Arg Pro Lys Ser Thr Pro Leu Ser Gln Pro Ser
    530                 535                 540

Ala Asn Gly Val Gln Thr Glu Gly Leu Asp Tyr Asp Arg Leu Lys Gln
545                 550                 555                 560

Asp Ile Leu Asp Glu Met Arg Lys Glu Leu Thr Lys Leu Lys Glu Glu
                565                 570                 575

Leu Ile Asp Ala Ile Arg Gln Glu Leu Ser Lys Ser Asn Thr Ala
            580                 585                 590

<210> SEQ ID NO 6
<211> LENGTH: 9
<212> TYPE: PRT
<213> ORGANISM: Artificial Sequence
<220> FEATURE:
<223> OTHER INFORMATION: SYNTHETIC PEPTIDE MTSTCD-01
```

```
<400> SEQUENCE: 6

Leu Pro Arg Gln Asn Gly Gln Leu Pro
1               5

<210> SEQ ID NO 7
<211> LENGTH: 9
<212> TYPE: PRT
<213> ORGANISM: Artificial Sequence
<220> FEATURE:
<223> OTHER INFORMATION: SYNTHETIC PEPTIDE MTSTCD-02

<400> SEQUENCE: 7

Leu Ala Arg Gln Asn Gly Gln Leu Pro
1               5

<210> SEQ ID NO 8
<211> LENGTH: 11
<212> TYPE: PRT
<213> ORGANISM: Artificial Sequence
<220> FEATURE:
<223> OTHER INFORMATION: SYNTHETIC PEPTIDE MTSTCD-03

<400> SEQUENCE: 8

Lys Ala Leu Pro Arg Gln Asn Gly Gln Leu Pro
1               5                   10

<210> SEQ ID NO 9
<211> LENGTH: 11
<212> TYPE: PRT
<213> ORGANISM: Artificial Sequence
<220> FEATURE:
<223> OTHER INFORMATION: SYNTHETIC PEPTIDE MTSTCD-04

<400> SEQUENCE: 9

Lys Ala Leu Ala Arg Gln Asn Gly Gln Leu Pro
1               5                   10

<210> SEQ ID NO 10
<211> LENGTH: 11
<212> TYPE: PRT
<213> ORGANISM: Artificial Sequence
<220> FEATURE:
<223> OTHER INFORMATION: HIV TAT PEPTIDE FRAGMENT 1

<400> SEQUENCE: 10

Tyr Ala Arg Ala Ala Ala Arg Gln Ala Arg Ala
1               5                   10

<210> SEQ ID NO 11
<211> LENGTH: 11
<212> TYPE: PRT
<213> ORGANISM: Artificial Sequence
<220> FEATURE:
<223> OTHER INFORMATION: HIV TAT PEPTIDE FRAGMENT 2

<400> SEQUENCE: 11

Tyr Gly Arg Lys Lys Arg Arg Gln Arg Arg Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: antithrombin III heparin-binding domain derived
      inhibitory peptide
```

```
<400> SEQUENCE: 12

Lys Ala Phe Ala Lys Leu Ala Ala Arg Leu Tyr Arg
1               5                   10

<210> SEQ ID NO 13
<211> LENGTH: 10
<212> TYPE: PRT
<213> ORGANISM: Artificial Sequence
<220> FEATURE:
<223> OTHER INFORMATION: antithrombin III heparin-binding domain derived
      inhibitory peptide

<400> SEQUENCE: 13

Phe Ala Lys Leu Ala Ala Arg Leu Tyr Arg
1               5                   10

<210> SEQ ID NO 14
<211> LENGTH: 20
<212> TYPE: PRT
<213> ORGANISM: Artificial Sequence
<220> FEATURE:
<223> OTHER INFORMATION: SYNTHETIC PEPTIDE MTST-10

<400> SEQUENCE: 14

Tyr Ala Arg Ala Ala Ala Arg Gln Ala Arg Ala Leu Pro Arg Gln Asn
1               5                   10                  15

Gly Gln Leu Pro
            20

<210> SEQ ID NO 15
<211> LENGTH: 20
<212> TYPE: PRT
<213> ORGANISM: Artificial Sequence
<220> FEATURE:
<223> OTHER INFORMATION: SYNTHETIC PEPTIDE MTST-11

<400> SEQUENCE: 15

Tyr Ala Arg Ala Ala Ala Arg Gln Ala Arg Ala Leu Ala Arg Gln Asn
1               5                   10                  15

Gly Gln Leu Pro
            20

<210> SEQ ID NO 16
<211> LENGTH: 22
<212> TYPE: PRT
<213> ORGANISM: Artificial Sequence
<220> FEATURE:
<223> OTHER INFORMATION: SYNTHETIC PEPTIDE MTST-12

<400> SEQUENCE: 16

Tyr Ala Arg Ala Ala Ala Arg Gln Ala Arg Ala Lys Ala Leu Pro Arg
1               5                   10                  15

Gln Asn Gly Gln Leu Pro
            20

<210> SEQ ID NO 17
<211> LENGTH: 22
<212> TYPE: PRT
<213> ORGANISM: Artificial Sequence
<220> FEATURE:
<223> OTHER INFORMATION: SYNTHETIC PEPTIDE MTST-13

<400> SEQUENCE: 17

Tyr Ala Arg Ala Ala Ala Arg Gln Ala Arg Ala Lys Ala Leu Ala Arg
1               5                   10                  15
```

Gln Asn Gly Gln Leu Pro
            20

<210> SEQ ID NO 18
<211> LENGTH: 20
<212> TYPE: PRT
<213> ORGANISM: Artificial Sequence
<220> FEATURE:
<223> OTHER INFORMATION: SYNTHETIC PEPTIDE MTST-14

<400> SEQUENCE: 18

Tyr Gly Arg Lys Lys Arg Arg Gln Arg Arg Leu Pro Arg Gln Asn
1               5                   10                  15

Gly Gln Leu Pro
            20

<210> SEQ ID NO 19
<211> LENGTH: 20
<212> TYPE: PRT
<213> ORGANISM: Artificial Sequence
<220> FEATURE:
<223> OTHER INFORMATION: SYNTHETIC PEPTIDE MTST-15

<400> SEQUENCE: 19

Tyr Gly Arg Lys Lys Arg Arg Gln Arg Arg Leu Ala Arg Gln Asn
1               5                   10                  15

Gly Gln Leu Pro
            20

<210> SEQ ID NO 20
<211> LENGTH: 22
<212> TYPE: PRT
<213> ORGANISM: Artificial Sequence
<220> FEATURE:
<223> OTHER INFORMATION: SYNTHETIC PEPTIDE MTST-16

<400> SEQUENCE: 20

Tyr Gly Arg Lys Lys Arg Arg Gln Arg Arg Lys Ala Leu Pro Arg
1               5                   10                  15

Gln Asn Gly Gln Leu Pro
            20

<210> SEQ ID NO 21
<211> LENGTH: 22
<212> TYPE: PRT
<213> ORGANISM: Artificial Sequence
<220> FEATURE:
<223> OTHER INFORMATION: SYNTHETIC PEPTIDE MTST-17

<400> SEQUENCE: 21

Tyr Gly Arg Lys Lys Arg Arg Gln Arg Arg Lys Ala Leu Ala Arg
1               5                   10                  15

Gln Asn Gly Gln Leu Pro
            20

<210> SEQ ID NO 22
<211> LENGTH: 23
<212> TYPE: PRT
<213> ORGANISM: Artificial Sequence
<220> FEATURE:
<223> OTHER INFORMATION: SYNTHETIC PEPTIDE MTST-18

<400> SEQUENCE: 22

Lys Ala Phe Ala Lys Leu Ala Ala Arg Leu Tyr Arg Lys Ala Leu Pro

```
                1               5                   10                  15
Arg Gln Asn Gly Gln Leu Pro
                20

<210> SEQ ID NO 23
<211> LENGTH: 23
<212> TYPE: PRT
<213> ORGANISM: Artificial Sequence
<220> FEATURE:
<223> OTHER INFORMATION: SYNTHETIC PEPTIDE MTST-19

<400> SEQUENCE: 23

Lys Ala Phe Ala Lys Leu Ala Ala Arg Leu Tyr Arg Lys Ala Leu Ala
1               5                   10                  15

Arg Gln Asn Gly Gln Leu Pro
                20

<210> SEQ ID NO 24
<211> LENGTH: 25
<212> TYPE: PRT
<213> ORGANISM: Artificial Sequence
<220> FEATURE:
<223> OTHER INFORMATION: SYNTHETIC PEPTIDE MTST-20

<400> SEQUENCE: 24

Lys Ala Phe Ala Lys Leu Ala Ala Arg Leu Tyr Arg Lys Ala Lys Ala
1               5                   10                  15

Leu Pro Arg Gln Asn Gly Gln Leu Pro
                20                  25

<210> SEQ ID NO 25
<211> LENGTH: 25
<212> TYPE: PRT
<213> ORGANISM: Artificial Sequence
<220> FEATURE:
<223> OTHER INFORMATION: SYNTHETIC PEPTIDE MTST-21

<400> SEQUENCE: 25

Lys Ala Phe Ala Lys Leu Ala Ala Arg Leu Tyr Arg Lys Ala Lys Ala
1               5                   10                  15

Leu Ala Arg Gln Asn Gly Gln Leu Pro
                20                  25

<210> SEQ ID NO 26
<211> LENGTH: 21
<212> TYPE: PRT
<213> ORGANISM: Artificial Sequence
<220> FEATURE:
<223> OTHER INFORMATION: SYNTHETIC PEPTIDE MTST-22

<400> SEQUENCE: 26

Phe Ala Lys Leu Ala Ala Arg Leu Tyr Arg Lys Ala Leu Pro Arg Gln
1               5                   10                  15

Asn Gly Gln Leu Pro
                20

<210> SEQ ID NO 27
<211> LENGTH: 21
<212> TYPE: PRT
<213> ORGANISM: Artificial Sequence
<220> FEATURE:
<223> OTHER INFORMATION: SYNTHETIC PEPTIDE MTST-23

<400> SEQUENCE: 27
```

```
Phe Ala Lys Leu Ala Ala Arg Leu Tyr Arg Lys Ala Leu Ala Arg Gln
1               5                   10                  15

Asn Gly Gln Leu Pro
            20

<210> SEQ ID NO 28
<211> LENGTH: 23
<212> TYPE: PRT
<213> ORGANISM: Artificial Sequence
<220> FEATURE:
<223> OTHER INFORMATION: SYNTHETIC PEPTIDE MTST-24

<400> SEQUENCE: 28

Phe Ala Lys Leu Ala Ala Arg Leu Tyr Arg Lys Ala Lys Ala Leu Pro
1               5                   10                  15

Arg Gln Asn Gly Gln Leu Pro
            20

<210> SEQ ID NO 29
<211> LENGTH: 23
<212> TYPE: PRT
<213> ORGANISM: Artificial Sequence
<220> FEATURE:
<223> OTHER INFORMATION: SYNTHETIC PEPTIDE MTST-25

<400> SEQUENCE: 29

Phe Ala Lys Leu Ala Ala Arg Leu Tyr Arg Lys Ala Lys Ala Leu Ala
1               5                   10                  15

Arg Gln Asn Gly Gln Leu Pro
            20

<210> SEQ ID NO 30
<211> LENGTH: 13
<212> TYPE: PRT
<213> ORGANISM: Artificial Sequence
<220> FEATURE:
<223> OTHER INFORMATION: MAPKAPK2/MK2 inhibitor derived from HSP25

<400> SEQUENCE: 30

Lys Lys Lys Ala Leu His Arg Gln Leu Gly Val Ala Ala
1               5                   10

<210> SEQ ID NO 31
<211> LENGTH: 14
<212> TYPE: PRT
<213> ORGANISM: Artificial Sequence
<220> FEATURE:
<223> OTHER INFORMATION: commercial Hayess and Benndorf peptide
      inhibitor of MK2/MAPKAPK2

<400> SEQUENCE: 31

Met Lys Lys Lys Ala Leu Asn Arg Gln Leu Gly Val Ala Ala
1               5                   10

<210> SEQ ID NO 32
<211> LENGTH: 20
<212> TYPE: PRT
<213> ORGANISM: Artificial Sequence
<220> FEATURE:
<223> OTHER INFORMATION: pS125 Mena epitope peptide
```

```
<400> SEQUENCE: 32

Cys Lys Lys Gly Pro Thr Leu Pro Arg Gln Asn Ser Gln Leu Pro Ala
1               5                   10                  15

Gln Val Ala Asn
            20
```